US009855300B2

(12) United States Patent
Da Silva Ferreira et al.

(10) Patent No.: US 9,855,300 B2
(45) Date of Patent: Jan. 2, 2018

(54) COMPOSITION AND METHOD TO IMPROVE THE THERAPEUTIC EFFECT OF STEM CELLS

(75) Inventors: Lino Da Silva Ferreira, Coimbra (PT); Dora Cristina Dos Santos Pedroso, Benavente (PT)

(73) Assignee: CRIOESTAMINAL, SAÚDE E TECNOLOGIA, SA., Cantanhede (PT)

( * ) Notice: Subject to any disclaimer, the term of this patent is extended or adjusted under 35 U.S.C. 154(b) by 1040 days.

(21) Appl. No.: 13/989,708

(22) PCT Filed: Nov. 28, 2011

(86) PCT No.: PCT/IB2011/055342
§ 371 (c)(1),
(2), (4) Date: Jan. 2, 2014

(87) PCT Pub. No.: WO2012/070032
PCT Pub. Date: May 31, 2012

(65) Prior Publication Data
US 2014/0147420 A1    May 29, 2014

(30) Foreign Application Priority Data
Nov. 26, 2010 (PT) .......................... 105406

(51) Int. Cl.
| A61K 35/51 | (2015.01) |
| C12N 5/0789 | (2010.01) |
| A61L 26/00 | (2006.01) |
| A61L 27/34 | (2006.01) |
| C12N 5/071 | (2010.01) |
| A61L 27/38 | (2006.01) |
| A61L 27/52 | (2006.01) |
| A61K 35/12 | (2015.01) |

(52) U.S. Cl.
CPC ............ *A61K 35/51* (2013.01); *A61L 26/008* (2013.01); *A61L 26/0057* (2013.01); *A61L 27/3834* (2013.01); *A61L 27/3886* (2013.01); *A61L 27/52* (2013.01); *C12N 5/0647* (2013.01); *C12N 5/0692* (2013.01); *A61K 2035/124* (2013.01); *C12N 2501/165* (2013.01); *C12N 2502/28* (2013.01); *C12N 2506/11* (2013.01); *C12N 2533/56* (2013.01)

(58) Field of Classification Search
None
See application file for complete search history.

(56) References Cited

U.S. PATENT DOCUMENTS

| 6,943,146 B2 * | 9/2005 | Jakubowski ....... A61K 38/1825 424/1.41 |
| RE39,192 E * | 7/2006 | MacPhee ............... A61K 38/48 424/198.1 |
| 2010/0028311 A1 * | 2/2010 | Motlagh ............. A61L 27/3834 424/93.7 |

OTHER PUBLICATIONS

Awad et al., Differential Healing Activities of CD34+ and CD14+ Endothelial Cell Progenitors, Arterioscler Thromb Vasc Biol. 2006;26:758-764.*
Ferreira, Vascular Progenitor Cells Isolated From Human Embryonic Stem Cells Give Rise to Endothelial and Smooth Muscle-Like Cells and Form Vascular Networks in Vivo, Circulation Research, 2007;101:286-294.).*
Smadja et al. (2008). Thrombin bound to a fibrin clot confers angiogenic and haemostatic properties on endothelial progenitor cells. *Journal of Cellular and Molecular Medicine*, 12(3), 975-986.
Kim et al. (2010). Human cord blood-derived endothelial progenitor cells and their conditioned media exhibit therapeutic equivalence for diabetic wound healing. *Cell Transplantation*, 19(12), 1635-1644.
Bompais et al. (2004). Human endothelial cells derived from circulating progenitors display specific functional properties compared with mature vessel wall endothelial cells. *Blood*, 103(7), 2577-2584.
Valbonesi et al. (2004). Cord blood (CB) stem cells for wound repair. Preliminary report of 2 cases. *Transfusion and Apheresis Science*, 30(2), 153-156.
Lonza. (2012). Clonetics™ endothelial cell medium products. Retrieved May 4, 2012 from http://bio.lonza.com/uploads/tx_mwaxmarketingmaterial/Lonza_BenchGuides_Clonetics_Endothelial_Cell_Medium_Products.pdf.
Pedroso et al. (2011). Improved survival, vascular differentiation and wound healing potential of stem cells co-cultured with endothelial cells. *PLoS ONE*, 6(1), e16114.
International Search Report and Written Opinion of the International Searching Authority, dated May 22, 2012 in connection with PCT International Application No. PCT/IB2011/055342, filed Nov. 28, 2011.

* cited by examiner

*Primary Examiner* — Taeyoon Kim
*Assistant Examiner* — Srikanth Patury
(74) *Attorney, Agent, or Firm* — John P. White; Cooper & Dunham LLP

(57) ABSTRACT

The invention relates to a composition and method used for injuries treatment with a surprisingly therapeutic effect. This composition comprises a population of cells derived from human umbilical cord blood which expresses one of the following markers: CD34, CD45, and CD31; a population of CD34$^+$ derived endothelial cells; and a biomimetic gel, preferably fibrin. The method for obtaining the composition comprises the derivation of a population of endothelial cells from CD34$^+$ cells and then a co-culture of a CD34$^+$ cells with CD34$^+$-derived endothelial cells within a biomimetic gel.

14 Claims, 18 Drawing Sheets

| Target gene | Primer sequence | |
|---|---|---|
| Human CD34 | Forward: TGAAGCCTAGCCTGTCACCT | (SEQ ID NO:1) |
| | Reverse: CGCACAGCTGGAGGTCTTAT | (SEQ ID NO:2) |
| Human vWF | Forward: ATGTTGTGGGAGATGTTTGC | (SEQ ID NO:3) |
| | Reverse: GCAGATAAGAGCTCAGCCTT | (SEQ ID NO:4) |
| Human VEGF | Forward: AGAAGGAGGAGGGCAGAATC | (SEQ ID NO:5) |
| | Reverse: ACACAGGATGGCTTGAAGATG | (SEQ ID NO:6) |
| Human PlGF | Forward: ACGTGGAGCTGACGTTCTCT | (SEQ ID NO:7) |
| | Reverse: CAGCAGGAGTCACTGAAGAG | (SEQ ID NO:8) |
| Human bFGF | Forward: AAGCAGGAGGATCGCTTGAG | (SEQ ID NO:9) |
| | Reverse: TGAAGCCTAGCCTGTCACCT | (SEQ ID NO:10) |
| Human GAPDH | Forward: AGCCACATCGCTCAGACACC | (SEQ ID NO:11) |
| | Reverse: GTACTCAGCGCCAGCATCG | (SEQ ID NO:12) |
| Mouse MPO | Forward: GCTACCGGCTCTCCTTCTT | (SEQ ID NO:13) |
| | Reverse: TTGCGAATGGTGATGTTGTT | (SEQ ID NO:14) |
| Mouse CD3ε | Forward: CACTCTGGGCTTGCTGATGG | (SEQ ID NO:15) |
| | Reverse: TCATAGTCTGGGTTGGGAACAGG | (SEQ ID NO:16) |
| Mouse TNFα | Forward: CATCTTCTCAAAATTCGAGTGACAA | (SEQ ID NO:17) |
| | Reverse: GGGAGTAGACAAGGTACAACCC | (SEQ ID NO:18) |
| Mouse GAPDH | Forward: ACCACAGTCCATGCCATCAC | (SEQ ID NO:19) |
| | Reverse: TCCACCACCCTGTTGCTGTA | (SEQ ID NO:20) |

[1] PCR conditions: initial denaturation step at 94°C for 5 min; 40 cycles of denaturation at 94°C for 30 sec, annealing at 60°C for 33 sec and extension at 72°C for 30 sec. At the end, a final 7 minutes extension at 72°C was performed.

Figure 16

COMPOSITION AND METHOD TO IMPROVE THE THERAPEUTIC EFFECT OF STEM CELLS

TECHNICAL FIELD OF THE INVENTION

The invention relates to a composition of a co-culture of human umbilical cord-derived $CD34^+$ cells with endothelial cells, derived from $CD34^+$ cells, in a biomimetic gel for injuries treatment.

BACKGROUND

This invention occurs with the need of more effective ways for the treatment of chronic wounds, especially in diabetic patients.

It is estimated that 15% of the diabetic patients have nonhealing foot ulcerations. In recent years, there have been efforts to develop new advanced methodologies to heal chronic wounds, including the use of topic growth factors or cell-based therapies. In case of stem cells, the treatment is based in the assumption that topical application of stem cells modulates the healing response. Recent data show that healthy adult stem/progenitor cells improve the healing of diabetic chronic wounds. It has been shown that peripheral blood-derived $CD34^+$ cells, but not $CD34^-$ cells, can accelerate the vascularization and healing of diabetic wounds (Schatteman G C et al, 2003). However, the vasculogenic potential of adult blood-derived cells appears to be reduced by diabetes. Recent studies tried to overcome this issue by using fetal (Invernici G et al., 2009) or adult mesenchymal stem cells (Tredget E E et al., 2007), yet, the isolation of stem cells from fetal aorta poses several problems for future clinical application, while mesenchymal stem cells isolated from diabetic patients might have impaired properties due to ageing and disease. In case of fetal aorta stem cells, the results indicate that the stem cells released factors (e.g. VEGF and IL-8), which stimulate angiogenesis and activate Wnt signaling, promoting the healing of diabetic ischemic ulcers.

Human umbilical cord blood (UCB) can be a potential source of healthy endothelial progenitor cells for the healing of chronic wounds in diabetic patients. These cells are obtained noninvasively, can be stored for more than 15 years without loosing biological properties, and they have low immunogenicity, which makes them an interesting candidate for allogeneic transplantation. Improvement in wound healing has been reported recently in two human non-diabetic patients who received topically UCB-derived $CD34^+$ cells in a fibrin gel (Dejana A M et al., 2004). Despite this potential, human umbilical cord blood stem cells have not been used for wound healing in diabetic patients, whose healing process is impaired or even inexistent. In this case, the stem cells may need the stimulation of bioactive agents and cell-cell interactions for survival and therapeutic effect. This is the focus of the present invention.

In the present patent, the therapeutic effect of $CD34^+$ cells or the combination of $CD34^+$ cells with $CD34^+$-derived ECs was tested in streptozotocin-induced diabetic mice, which have previously been used to study the effect of cell-based therapies on wound healing (Invernici G et al., 2009, Wu Y, 2008). Importantly, no study has documented the regenerative potential of UCB-derived $CD34^+$ cells in the context of diabetic wounds. Here, we show that the transplantation of $CD34^+$ cells together with $CD34^+$-derived ECs, but not $CD34^+$ cells alone, in fibrin gels enhances wound healing, compared to wounds covered with gel alone or PBS. A substantial fraction of cells (more than 90%) died over a 3 day period. This is in line with other studies showing a dramatic decline of stem cells at the injury site (Invernici G et al., 2009)]. Even so, a therapeutic benefit was observed over the 10 day period in our study, likely due to factors secreted by both cells, which increased neovascularization and decreased the inflammatory reaction. Our results show that cytokines IL-10 and IL-17 are only secreted when both cells are co-cultured. IL-10 is a potent immunosuppressant of monocyte/macrophage functions, inhibiting the production of pro-inflammatory cytokines. Our Multiplex results also indicate that the level of INF-α, a pro-inflammatory cytokine, was lower for wounds treated with $CD34^+$ cells and ECs, or only $CD34^+$ cells encapsulated in fibrin gel.

Regarding prior art, there are several patents in the field of Regenerative Medicine that use some of the components of the present invention, but provide methods and compositions that are substantially different. For example, the patent application entitled "Using of scaffold comprising fibrin for delivery of stem cells" (US2010/0028311A1) provides, in part, compositions and methods for treating ischemia in a subject in need thereof. The method consisted in the administration of a fibrin scaffold or fibrin clot comprising stem cells ($CD34^+$ cells). However, the invention did not describe methods to improve the viability, vascular differentiation and therapeutic effect of the $CD34^+$ cells.

SUMMARY

"Injury" refers to damage to a biological organism which can be classified on various bases. It includes traumatic injury, injury from infection, metabolic injury (complication of diabetes), injuries caused by ischemic and vascular diseases and injury from a toxin or as adverse effect of pharmaceutical drug, injury due to autoimmunity, cancer and disease. Include, in addition, wounds, brain injury, spinal cord injury, nerve injury and cell damage.

"$CD34^+$ cells" refers to cells expressing CD34 antigen. This antigen is a single-chain transmembrane glycoprotein expressed in several cells including human hematopoietic stem and progenitor cells, vascular endothelial cells, embryonic fibroblasts and some cells in fetal and adult nervous tissue. The $CD34^+$ cells described in the present invention were isolated from human cord blood by the use of magnetic beads containing the antibody anti-human CD34 clone AC136 which recognizes a class III epitope of the CD34 antigen. These cells were then differentiated into endothelial cells.

"Growth Factors" refers to chemicals that regulate cellular metabolic and intracellular signaling processes, including but not limited to differentiation, proliferation, synthesis of various cellular products, and other metabolic activities. Growth factors may include several families of, chemicals, including but not limited to cytokines, eicosanoids, and differentiation factors.

"Endothelial cells" refers to cells that have typical cobblestone morphology. These cells can be distinguished from other cells by the expression of one or more of the following endothelial cell markers: CD31, CD34, KDR/Flk-1, vascular endothelial cadherin (VE-CAD) and von Willebrand factor (vWF). These cells have also the ability to form vascular networks when seeded on a gelatinous protein mixture secreted by Engelbreth-Holm-Swarm (EHS) mouse sarcoma cells, for example Matrigel™ 3D matrix and to incorporate DiI-labeled acetylated low-density lipoprotein (DiI-Ac-LDL).

"Fetal bovine serum" or FBS refers to the portion of plasma remaining after coagulation of blood, during which process the plasma protein fibrinogen is converted to fibrin and remains behind in the clot.

The present invention relates to a composition comprising:
- a population of cells derived from human umbilical cord blood which expresses one of the following markers: $CD34^+$, CD45, and CD31;
- a population of $CD34^+$ derived endothelial cells, which expresses at least one of the following markers: vWF, Flk-1/KDR, CD31, vascular endothelial-cadherin, metabolize Ac-LDL;
- a biomimetic gel;

a therapeutically effective amount of all the previous components. In a preferred embodiment the composition could further comprise an adequate amount of excipient.

In a preferred embodiment of the compositions disclosed by the present invention, the biomimetic gel is at least one of the followings: fibrin, hyaluronic acid, alginate, agarose, collagen or PEG derivatives. In a more preferred embodiment the fibrin gel comprises a fibrinogen at a final concentration from 1-100 mg/ml and thrombin at a final concentration from 1-500 U/ml, an even more preferred embodiment the fibrin gel comprises a fibrinogen concentration of 10-30 mg/ml and thrombin at a final concentration from 2-50 U/ml.

In more preferred embodiment of the compositions disclosed by the present invention, the population of the said $CD34^+$ comprises autologous cells, allogeneic cells or mixtures thereof.

Another preferred embodiment of the compositions disclosed by the present invention, the compositions above described comprise:
- $CD34^+$ cells in a concentration from $10 \times 10^2$ to $10 \times 10^6$ cells per 1 mL of fibrin gel,
- and the ratio of $CD34^+$ cells to $CD34^+$-derived endothelial cells is between 10:1 to 5:1.

More preferably, the $CD34^+$ cells are present in a concentration of $4.0 \times 10^6$ cells per 1 mL of fibrin gel.

Another more preferred embodiment of the compositions disclosed by the present invention, the ratio of CD34+ cells to $CD34^+$-derived endothelial cells in the compositions above described is between 0.5:1-1:1, more preferably 3:1.

In other more preferred embodiment of the compositions disclosed by the present invention, the compositions above described further comprises a member of the group consisting of collagen I, collagen IV, laminin, fibrin, fibronectin, proteoglycans, glycoproteins, glycoaminoglycans, proteinases, collagenases, chemotactic agents, growth factors, among others. In a more preferably aspect the growth factor can be selected from VEGF, VEGF165, PDGF, angiopoietin-Ang, ephrin-Eph, fibroblast growth factor-FGF, placental growth factor-PlGF, transforming growth factor β-1 [(TGF)-β1], cytokines, erythropoietin, thrombopoietin, transferring, insulin, stem cell factor (SCF), granulocyte colony-stimulating factor (G-CSF) and granulocyte-macrophage colony stimulating factor (GM-CSF) to form a mixture and implantation of the mixture into an animal, or mixtures thereof, among others. In a more preferred aspect the concentration of VEGF165 can be 30-100 ng/mL, preferably 50 ng/mL.

Another preferred embodiment of the compositions disclosed by the present invention, the fibrinogen of the fibrin gel of the compositions above can be isolated from a sample of patient's blood.

Another more preferred embodiment of the compositions the present invention could be a pharmaceutical, a medical or a cosmetic composition that could be used in medicine or in cosmetic industry. More specifically, in treatment of wound in diabetic mammal or in the treatment of ischemic and vascular diseases. An even more preferable embodiment the compositions could be a topic formulation or an injectable formulation.

Another aspect of the present invention is described a method for obtaining the composition above described, by the following steps:
- comprising isolation of $CD34^+$ cells from cord blood mononuclear cells;
- endothelial differentiation using $CD34^+$ cells isolated from cord blood in adequate medium; namely a medium comprising endothelial growth medium-2-EGM-2; Lonza, FBS and $VEGF_{165}$; more preferably wherein the cells seeding density in the medium is $10 \times 10^4$ cells per $cm^2$;
- combining the $CD34^+$ cells with endothelial cells differentiated from $CD34^+$ within a biomimetic gel, preferably fibrin.

In a preferred embodiment, the differentiation of $CD34^+$ cells into $CD34^+$-derived endothelial cells is performed at cell density of $50 \times 10^3$ to $20 \times 10^4$ cells/$cm^2$, preferably $10 \times 10^4$ to $15 \times 10^4$ cells/$cm^2$.

Other preferred embodiment of the compositions disclosed by the present invention, the population of $CD34^+$ cells is differentiated into endothelial cells after exposure to a concentration of $VEGF_{165}$ that is in the range about 20 ng/mL to 100 ng/mL.

A more preferred embodiment of the compositions disclosed by the present invention, the population of $CD34^+$ cells is differentiated into endothelial cells after exposure to $VEGF_{165}$ and a concentration of FBS between 15% to 20% (v/v), preferably 18% (v/v).

Another aspect of the present invention also described a method for obtaining the composition above described an in the absence of $CD34^+$-derived endothelial cells, comprising the isolation of $CD34^+$ cells from cord blood mononuclear cells in a medium supplemented with IL-10, IL-17, with an adequated biomolecule able to activate mitogen activated protein kinase (MAPK)/extracellular signal regulated kinase 1/2 (ERK 1/2) pathways, or mixtures thereof.

GENERAL DESCRIPTION OF THE INVENTION

The invention relates to a composition and method used for injuries treatment. This composition comprises a co-culture of Umbilical Cord Blood (UCB)-derived $CD34^+$ cells encapsulated in a biomimetic gel to promote the healing, for example, of diabetic wounds and ischemic and vascular diseases. To enhance the therapeutic effect of $CD34^+$ cells, they were co-cultured with endothelial cells (ECs) derived from $CD34^+$ cells. $CD34^+$-derived ECs co-cultured with $CD34^+$ cells improve surprisingly cell survival and contribute to the differentiation of CD34+ cells into ECs. We further show that the co-culture system, but not $CD34^+$ cells or $CD34^+$-derived ECs alone, can improve the healing kinetics in a diabetic animal model. In addition this co-culture approach might be used in other contexts to enhance the efficacy of stem cells.

The method is formed by two steps: first, stem cells ($CD34^+$ cells) are differentiated into endothelial cells; second, the $CD34^+$-derived endothelial cells are mixed with stem cells ($CD34^+$ cells) in a fibrin gel precursor solution.

This cell suspension can then be injected in vivo, gelify in situ, and contribute for the regeneration of ischemic tissues.

DESCRIPTION OF THE FIGURES

The following figures provide preferred embodiments for illustrating the description and should not be seen as limiting the scope of invention.

FIG. 16—Primer sequences used for qPCR.

DETAILED DESCRIPTION OF THE INVENTION

Figure 1A:
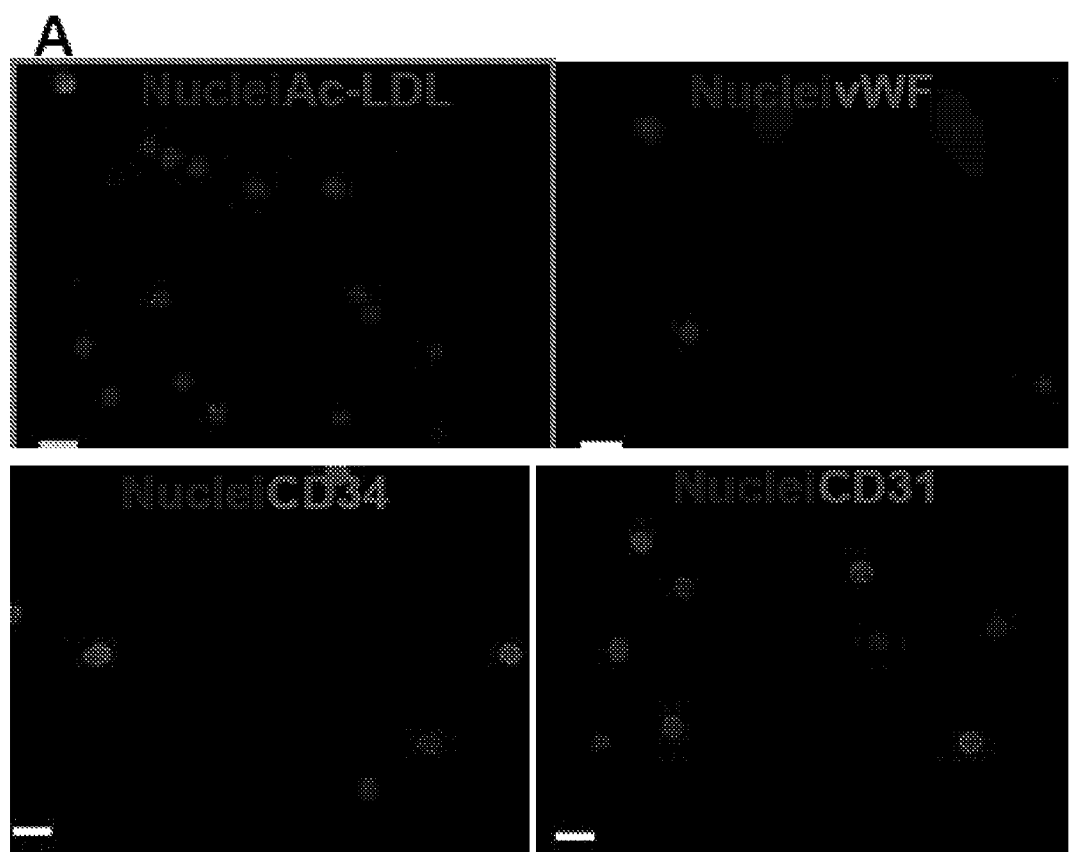
FIG. 1A—Expression of vascular markers in undifferentiated $CD34^+$ cells and their endothelial progenies. A) Immunofluorescence results for undifferentiated $CD34^+$ cells. Bar corresponds to 20 μm.
Figure 1B:
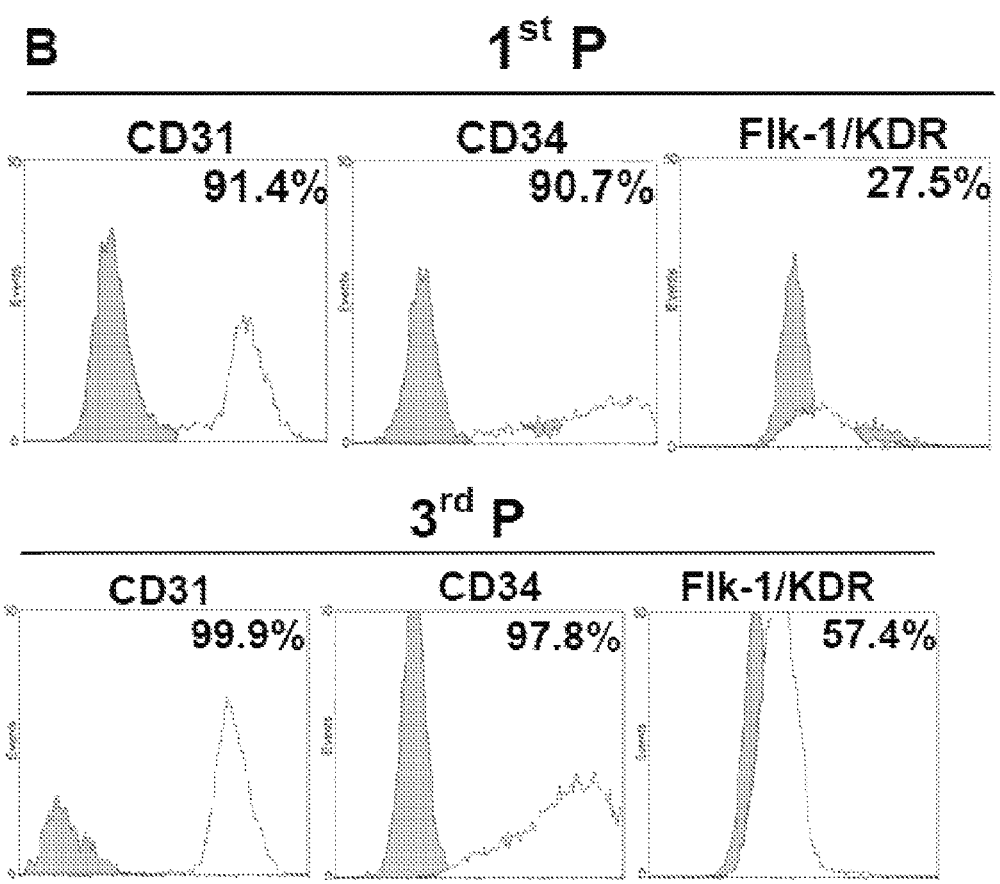
FIG. 1B—Expression of vascular markers in undifferentiated $CD34^+$ cells and their endothelial progenies. B) FACS analysis of $CD34^+$-derived ECs at passage 1 (1st P) and 3 (3rd P). Percent of positive cells were calculated based in the isotype controls (grey plot) and are shown in the histogram plots.
Figure 2A:
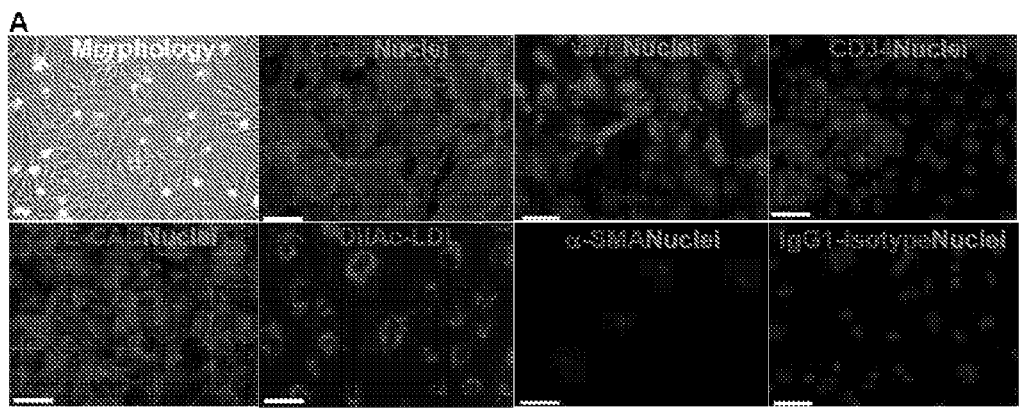
FIG. 2A—Characterization of $CD34^+$-derived ECs. A) Immunofluorescence analysis. Bar corresponds to 40 μm.
Figure 2B:
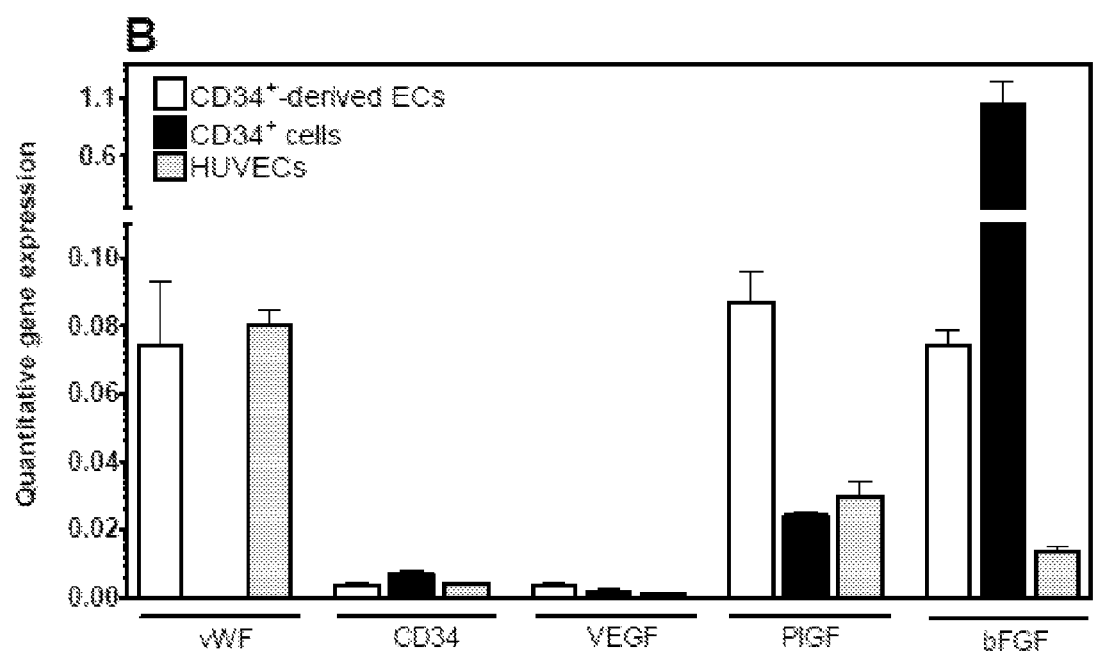
FIG. 2B—Characterization of $CD34^+$-derived ECs. B) Quantitative RT-PCR analysis. Results are average±SD, n=4.
Figure 2C:
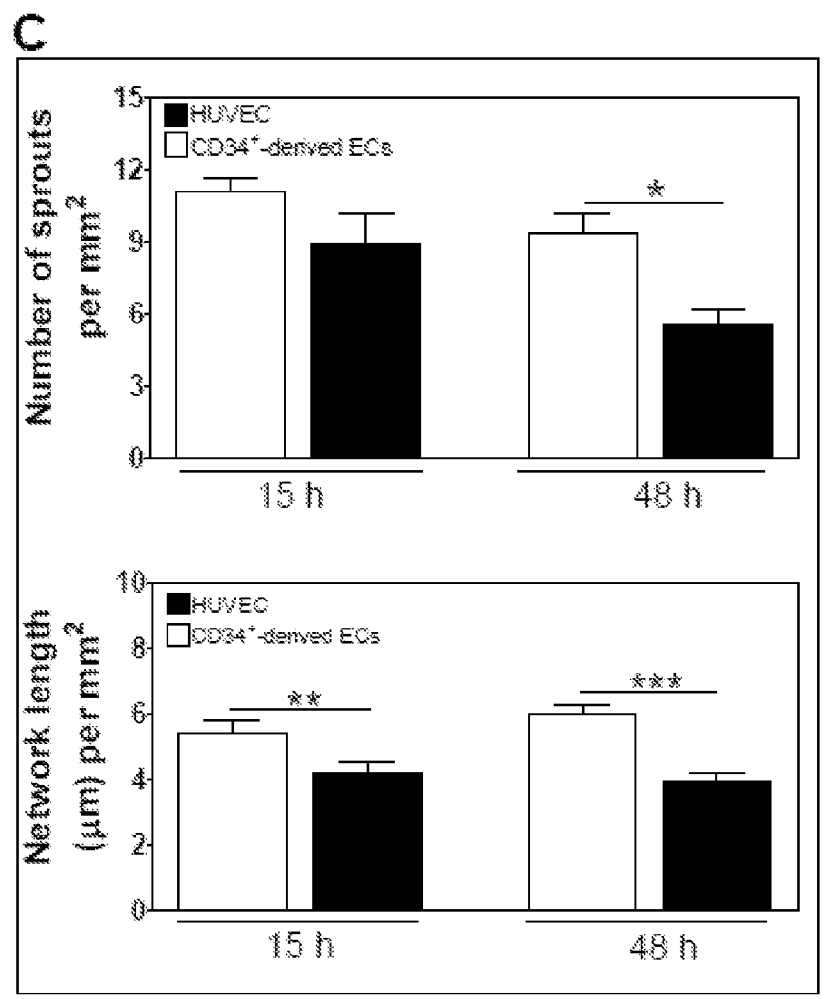
FIG. 2C—Characterization of $CD34^+$-derived ECs. C) Quantification of cord length and number of sprouts at 48 h. Counts were performed using an objective of ×10. Results are average±SD, n=3. *, , * denote statistical significance ($P<0.05$, $P<0.01$, $P<0.001$, respectively).
Figure 2D:
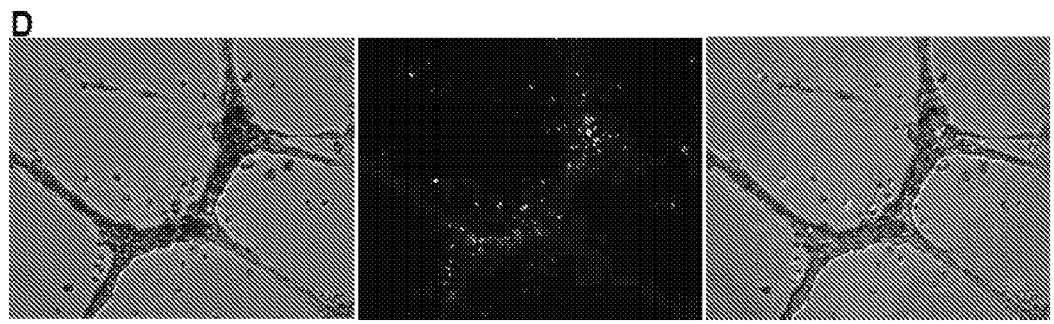
FIG. 2D—Characterization of $CD34^+$-derived ECs. D) Formation of cord-like structures by $CD34^+$-derived ECs (red) and $CD34^+$ cells (green) when placed in a gelatinous protein mixture secreted by Engelbreth-Holm-Swarm (EHS) mouse sarcoma cells—Matrigel™—for 24 h. Bar corresponds to 40 μm.
Figure 3:
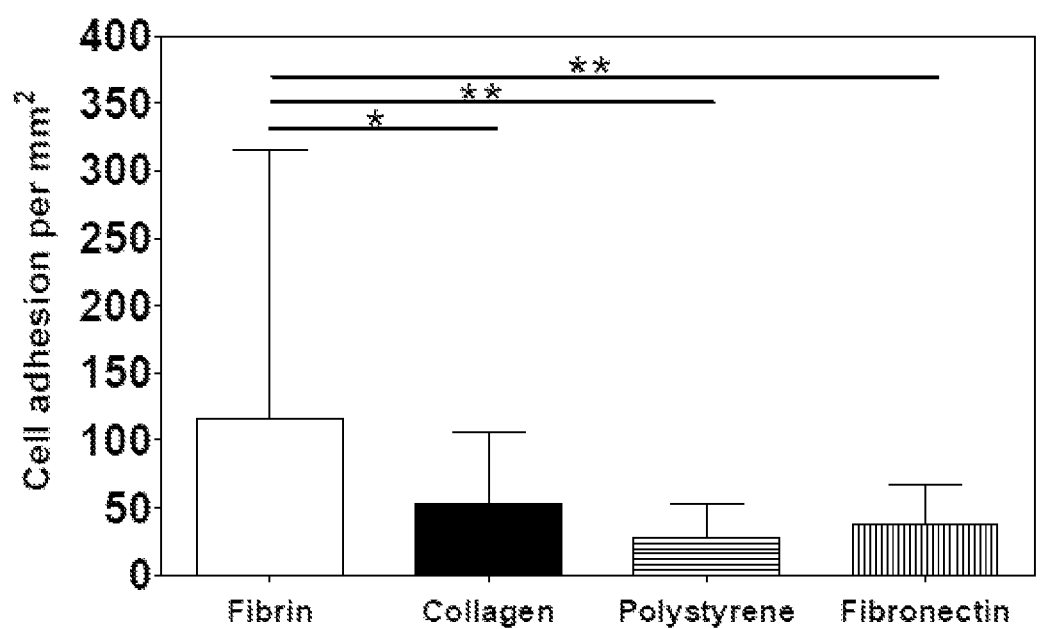
FIG. 3—Adhesion of $CD34^+$ cells to different substrates. $CD34^+$ cells were plated on 24-well plates coated with fibrin gel, type I collagen gel (2.5 mg/mL) and fibronectin (50 μg/mL). Polystyrene culture wells were used as control. Results are average±SD, n=6. * and ** denote statistical significance ($P<0.05$ and $P<0.01$, respectively).
Figure 4:
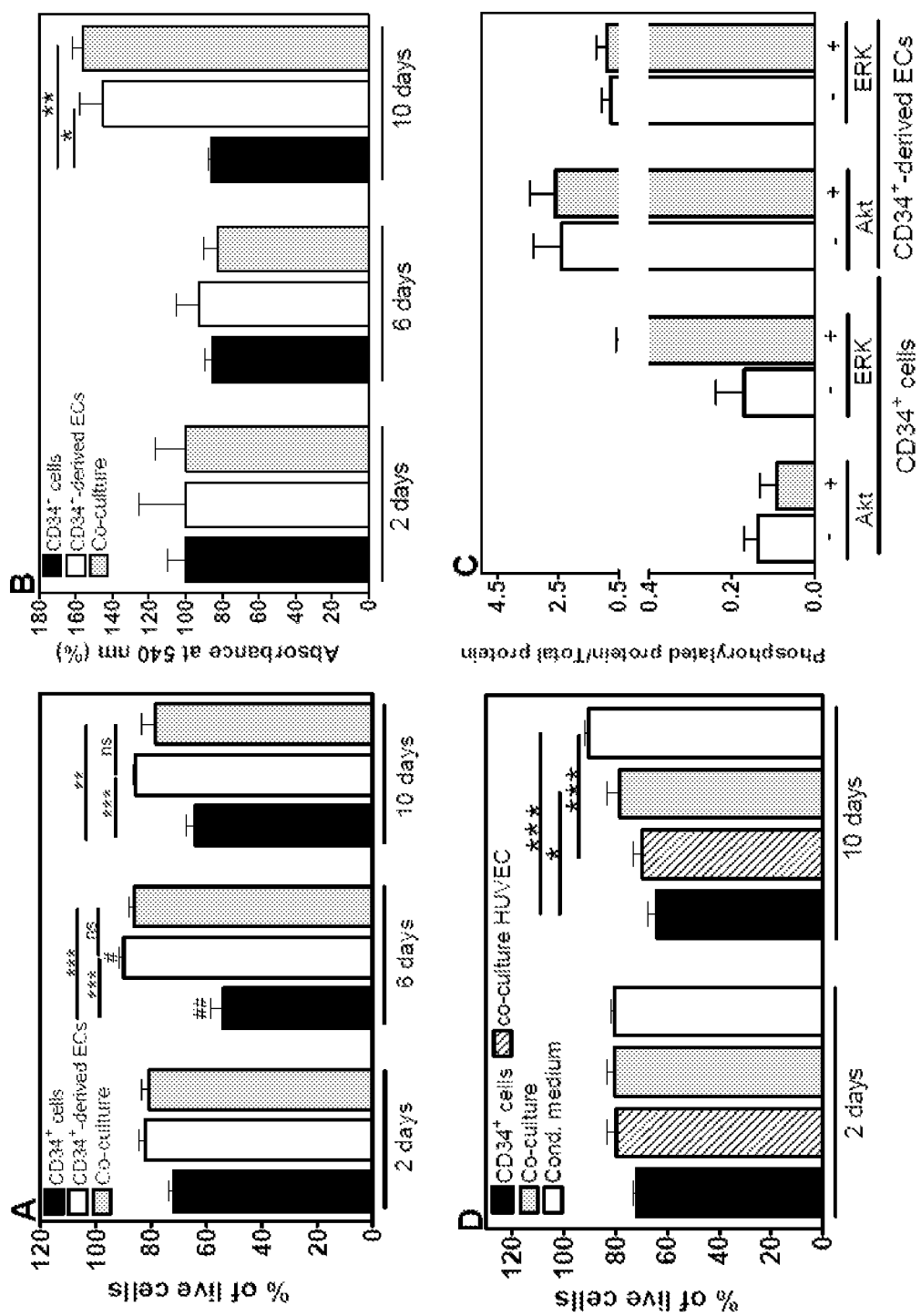
FIG. 4—Viability of encapsulated cells. A) Viability of encapsulated cells, as assessed by a LIVE/DEAD assay. Results are average±SD, n=3. B) Mitochondrial metabolic activity of encapsulated cells. Results are average±SD, n=6. Each absorbance at 540 nm was normalized by day 2 absorbance. C) Viability of encapsulated cells, as quantified by a LIVE/DEAD assay. Results are average±SD, n=3. In all figures, * denote statistical significance within time group: * $P<0.05$, $P<0.01$, * $P<0.001$. # denotes statistical significance between time groups comparing the respective control/treatment groups: # $P<0.05$, ## $P<0.01$. D) Phosphorylated Akt/total Akt and phosphorylated ERK/total ERK ratios assessed by a Bio-Plex phosphoprotein detection assay. Results are average±SD, n=3.
Figure 5:
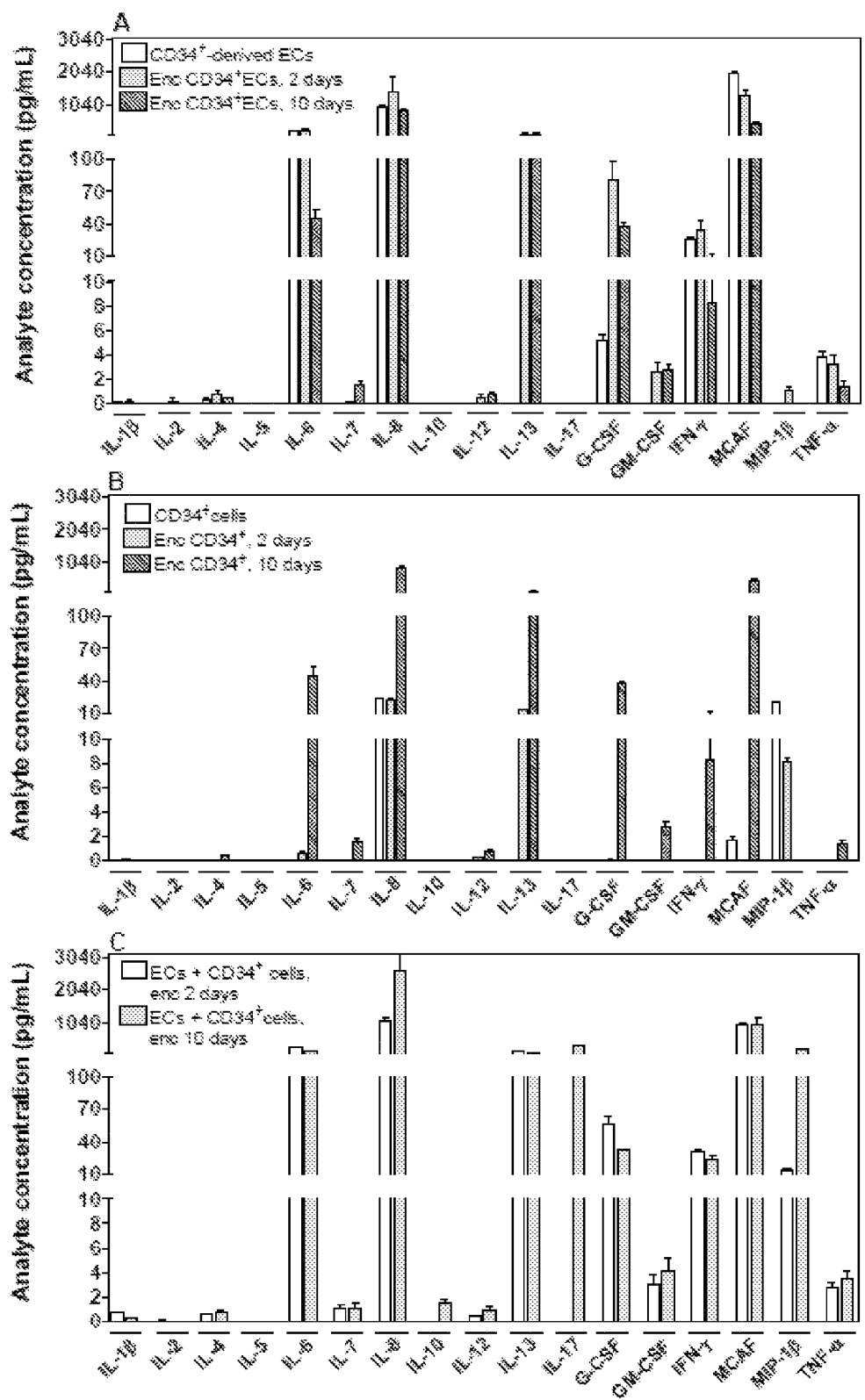
FIG. 5—Multiplex cytokine analysis. Analysis of cytokines secreted by (A) $CD34^+$-derived ECs grown on tissue culture polystyrene or encapsulated in fibrin gels for 2 or 10 days, (B) $CD34^+$ cells grown on tissue culture polystyrene or encapsulated in fibrin gels for 2 or 10 days and (C) co-culture of $CD34^+$ and $CD34^+$-derived ECs encapsulated in fibrin gels for 2 or 10 days. Cell media was collected after being in contact with the cells for 2 days. Results are average±SD, n=3.
Figure 6:
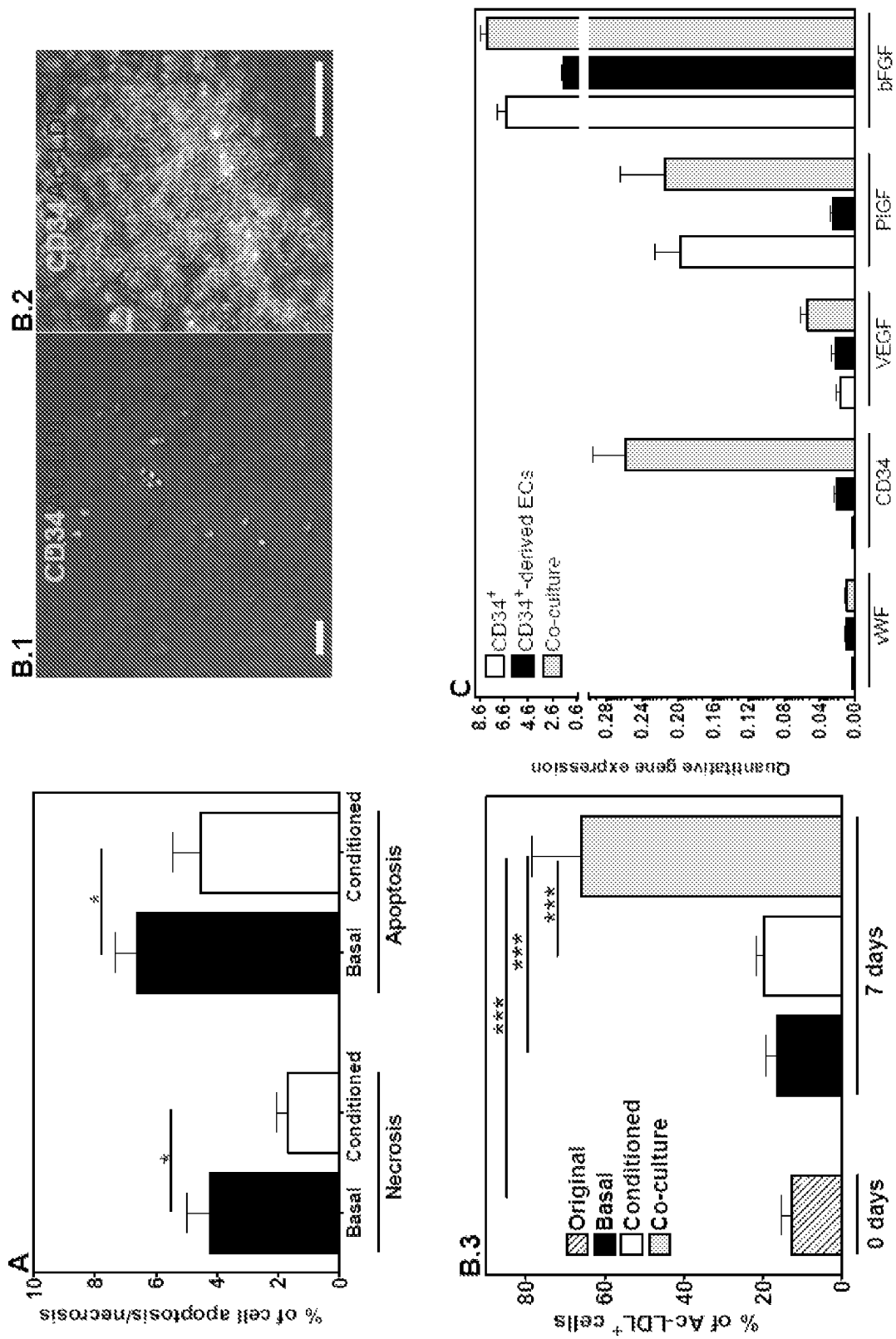
FIG. 6—Viability and differentiation of $CD34^+$ cells cultured on top of fibrin gels. A) Apoptosis and necrosis of $CD34^+$ cells cultured on top of fibrin gels, in EGM-2 medium or EGM-2 medium conditioned by $CD34^+$-derived ECs. Results are average±SD, n=3 (using a ×10 objective). B) $CD34^+$ cell differentiation on top of fibrin gels for 7 days in the absence (B.1) or in the presence (B.2) of $CD34^+$-derived ECs. B.3 shows the percentage of cells able to uptake Ac-LDL. C) Quantitative RTPCR analysis of $CD34^+$, $CD34^+$-derived ECs, or a co-culture of both cells. Results are average±SD, n=4. In all figures, * denote statistical significance: * $P<0.05$, $P<0.01$, * $P<0.001$.
Figure 7A:
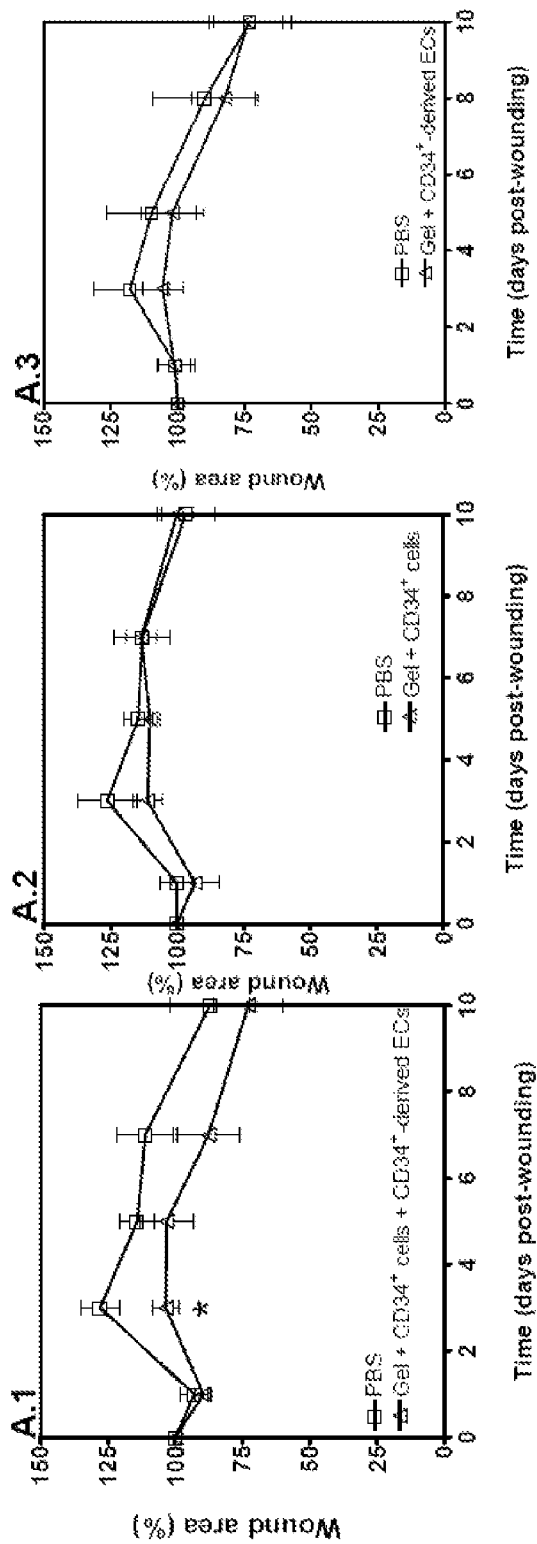
FIG. 7A—Regenerative effect of encapsulated $CD34^+$ and $CD34^+$-derived ECs on diabetic wounds. A) Wound closure (relatively to initial wound area) in diabetic mice treated by topical application of $1\times10^5$ $CD34^+$ cells and $0.35\times10^5$ $CD34^+$-derived ECs (A.1), $CD34^+$ cells (A.2) or $CD34^+$-derived ECs (A.3), encapsulated in fibrin gels. Control wounds received a saline solution (PBS) only. Results are average±SEM, n=6. * denotes statistical significance ($P<0.05$).
Figure 7:
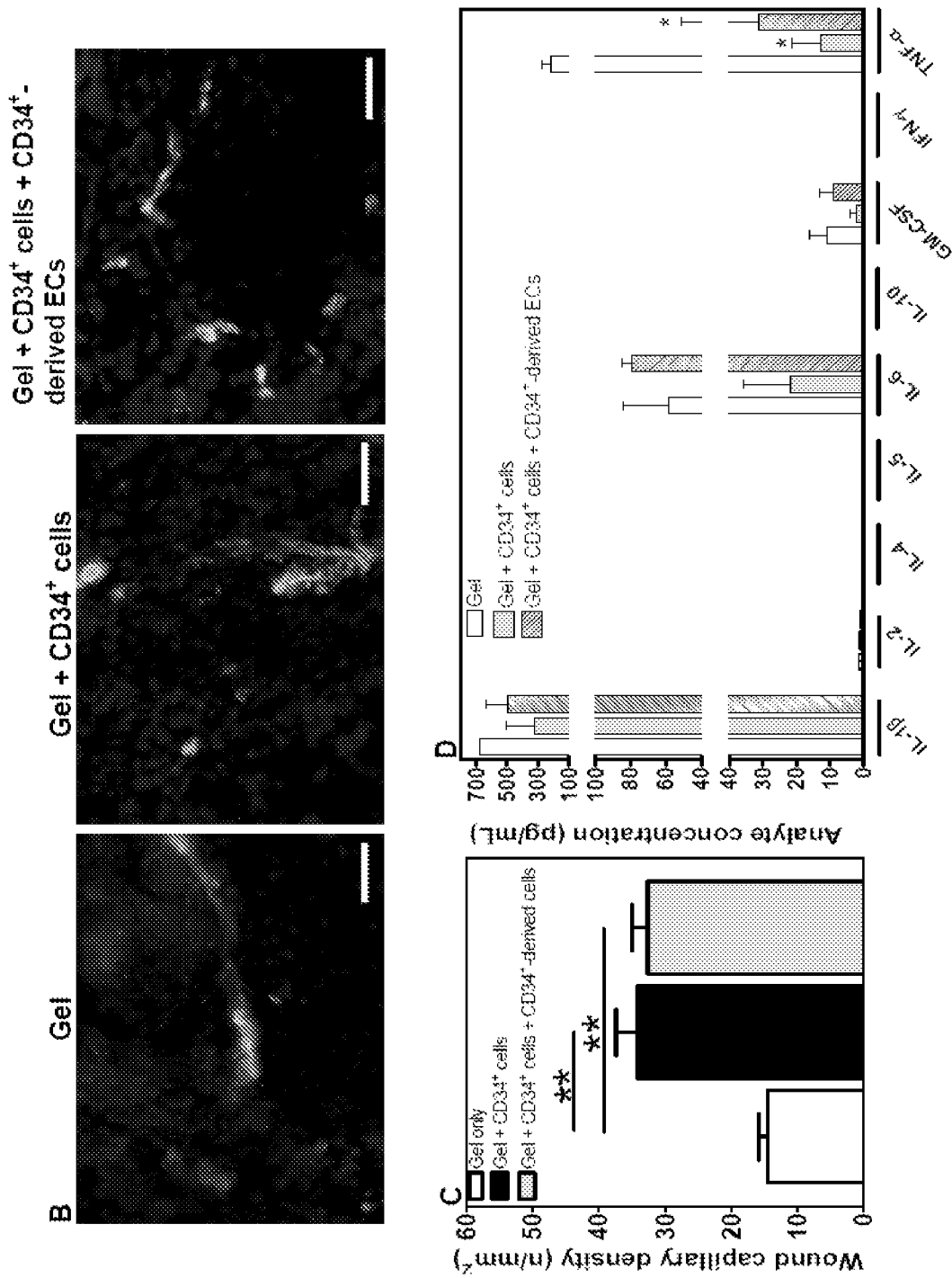
FIG. 7B—Regenerative effect of encapsulated $CD34^+$ and $CD34^+$-derived ECs on diabetic wounds. B) Representative images of vWF immunostaining. Scale bar represents 50 μm. C) Quantification of wound capillary per $mm^2$, based in the vWF immunostaining results. Results are average±SEM, n=3.** denotes statistical significance ($P<0.001$). D) Cytokine expression on mouse wound samples excised 3 days post-wounding, as determined by a Bio-Plex mouse cytokine assay. Wounds had been treated by topical application of $CD34^+$ cells or $CD34^+$-derived ECs encapsulated in fibrin gels. Control wounds received fibrin gel alone. Results are average±SD, n=3.
Figure 8:
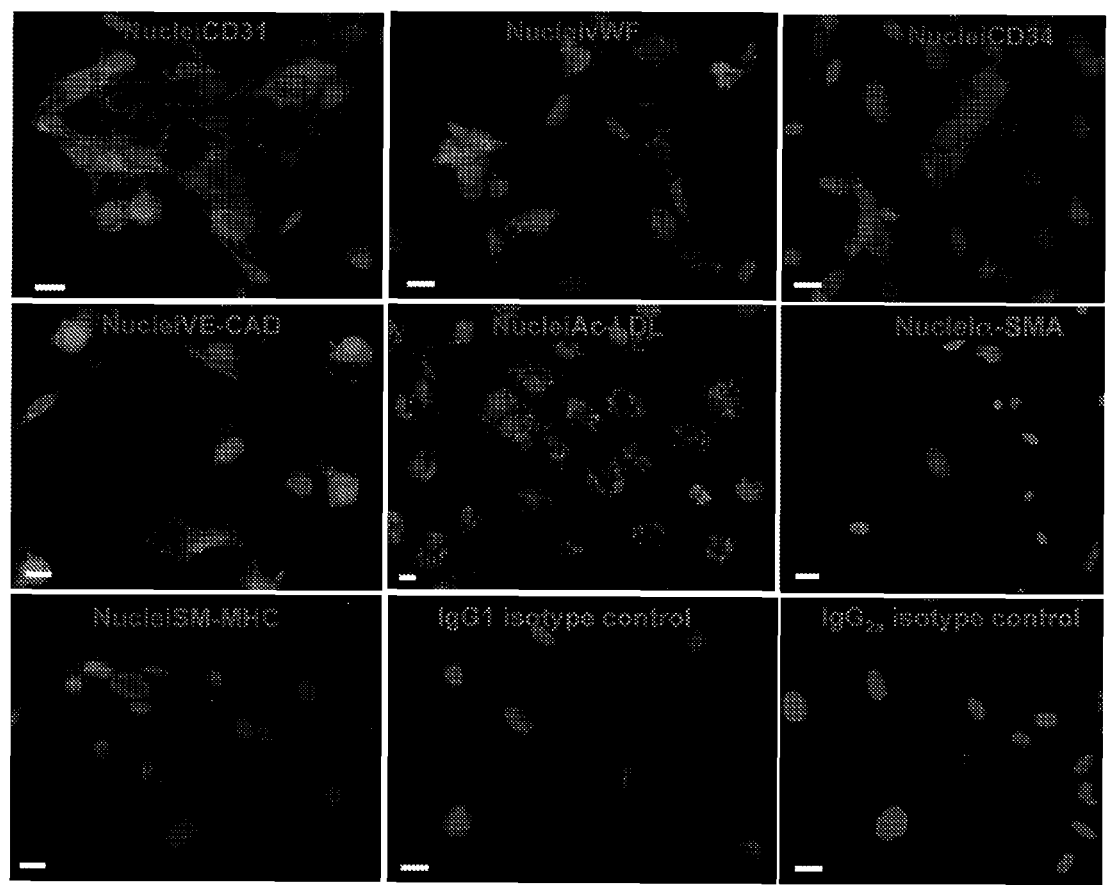
FIG. 8—Characterization of HUVECs by immunofluorescence. Cells express high levels of CD31, vWF and VE-CAD, low levels of CD34, have the ability to uptake Ac-LDL and do not express typical smooth muscle cell markers such as α-SMA and SM-MHC. Bar corresponds to 20 μm.
Figure 9:
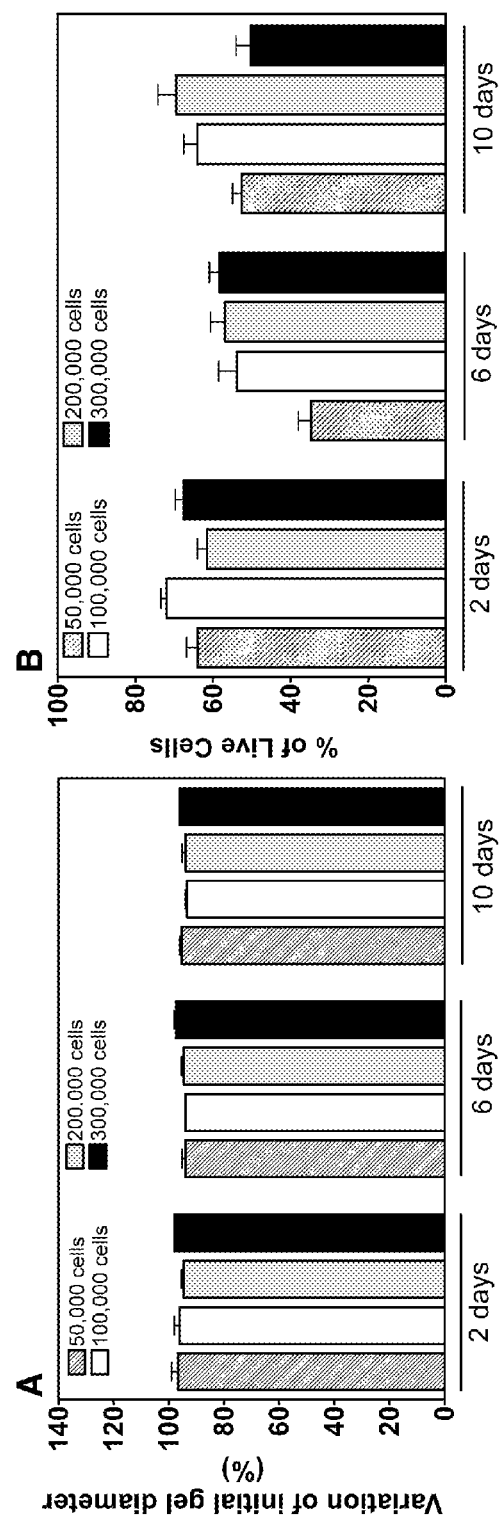
FIG. 9—Ability of vascular cells to form networks in a gelatinous protein mixture secreted by Engelbreth-Holm-Swarm (EHS) mouse sarcoma cells—Matrigel™. $CD34^+$-derived ECs as well as HUVECs form cords when seeded in the said Matrigel™ for 48 h. Bar corresponds to 40 μm.
Figure 10:
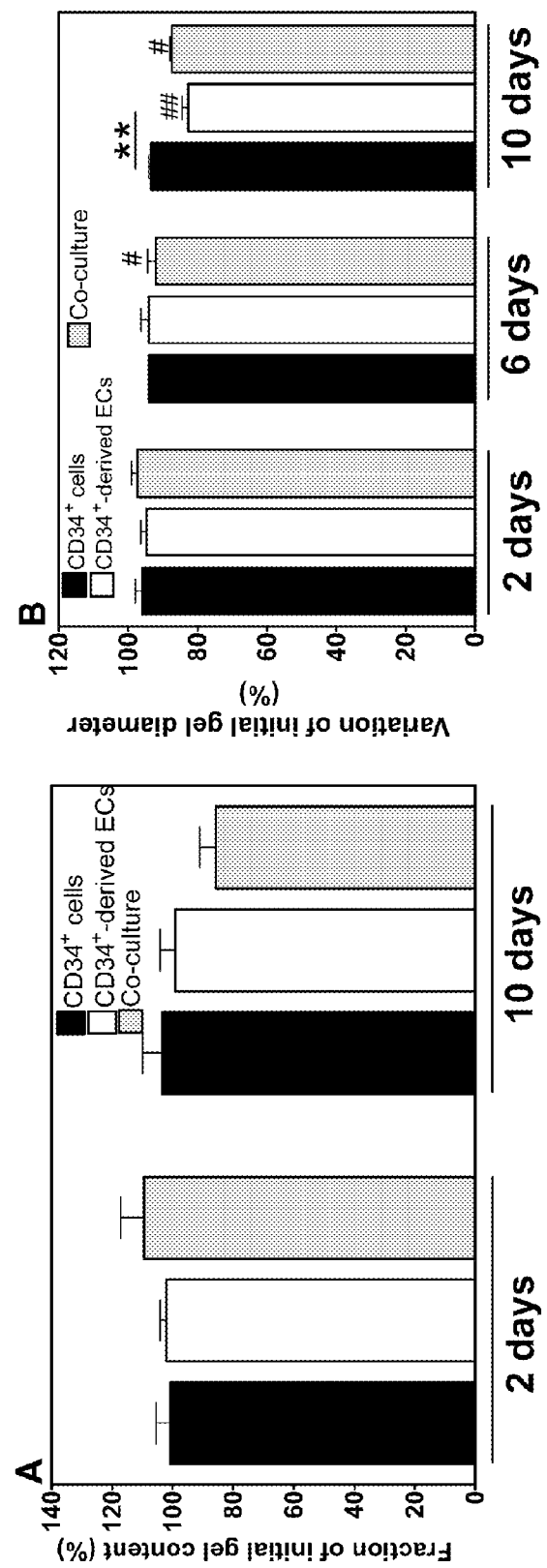
FIG. 10—Effect of cell number on the gel contraction and in the viability of $CD34^+$ cells encapsulated in fibrin gels. A) Variation of gel diameter over time for constructs having a defined number of $CD34^+$ cells. For all experimental groups, low gel contraction is observed after 10 days. B) Viability of encapsulated $CD34^+$ cells, as assessed by a LIVE/DEAD assay. The assay was performed at days 2, 6 and 10. Cell viability is affected by the number of cells encapsulated in the gel. Results are average±SD, n=3 (3 readings per construct).
Figure 11:
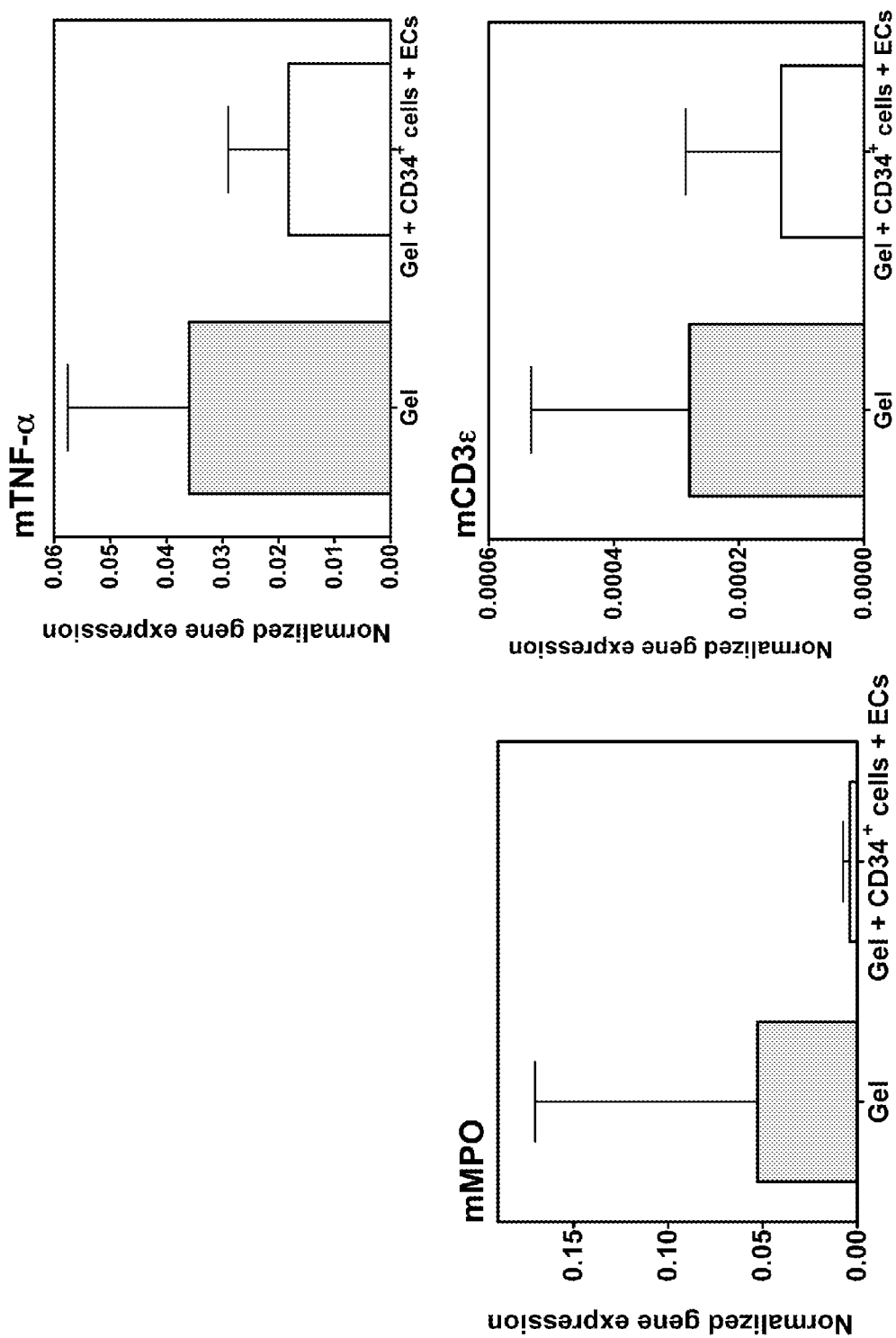
FIG. 11—Degradation of fibrin gels containing cells. A) Degradation of fluorescently-labeled fibrin gels containing $1\times10^5$ $CD34^+$ cells, or $0.35\times10^5$ $CD34^+$-derived ECs, or a co-culture of both cells at these numbers. Low degradation of fibrin gels is observed for all experimental groups. B) Variation of gel diameter over time. Low gel contraction is observed after 10 days. Results are average±SD, n=3. * denotes statistical significance within time group: ** $P<0.01$. # denotes statistical significance between time groups comparing the respective control/treatment groups: # $P<0.05$, ## $P<0.01$.
Figure 12:
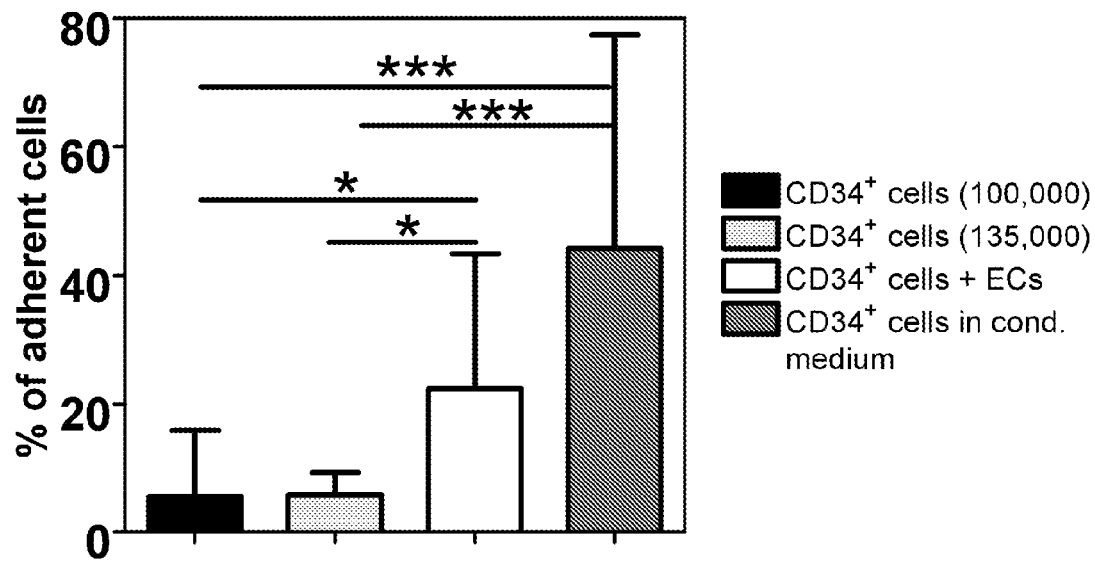
FIG. 12—Expression of inflammation-related genes by quantitative RT-PCR, on mouse wound skin biopsies at day 3. Wounds had been treated by topical application of fibrin gel containing $1\times10^5$ $CD34^+$ cells and $0.35\times10^5$ $CD34^+$-derived ECs. Control wounds were covered with gel only. Results are average±SD, n=9.
Figure 13:
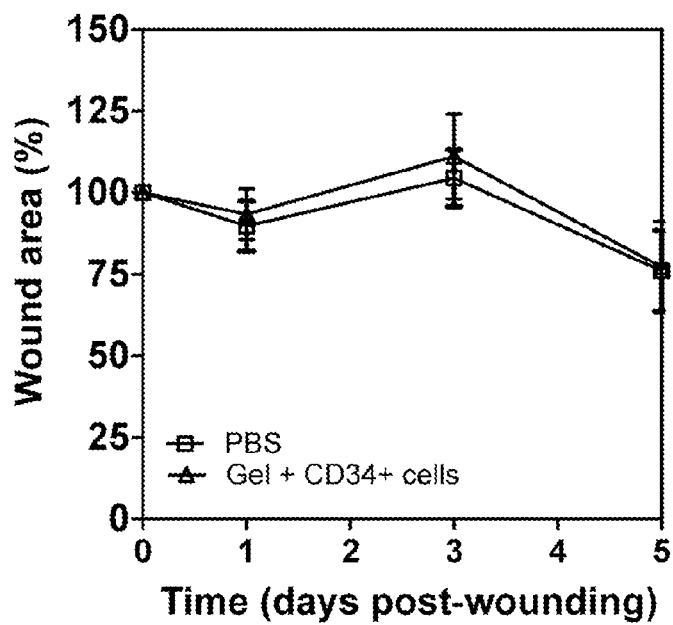
FIG. 13—Regenerative effect of CD34+ cells encapsulated in fibrin gels on diabetic wounds. Wound closure (relatively to initial wound area) in diabetic mice treated by topical application of $1.35\times10^5$ CD34+ cells encapsulated in fibrin gels. Control wounds received a saline solution (PBS) only. Results are average±SEM, n=5.
Figure 14:
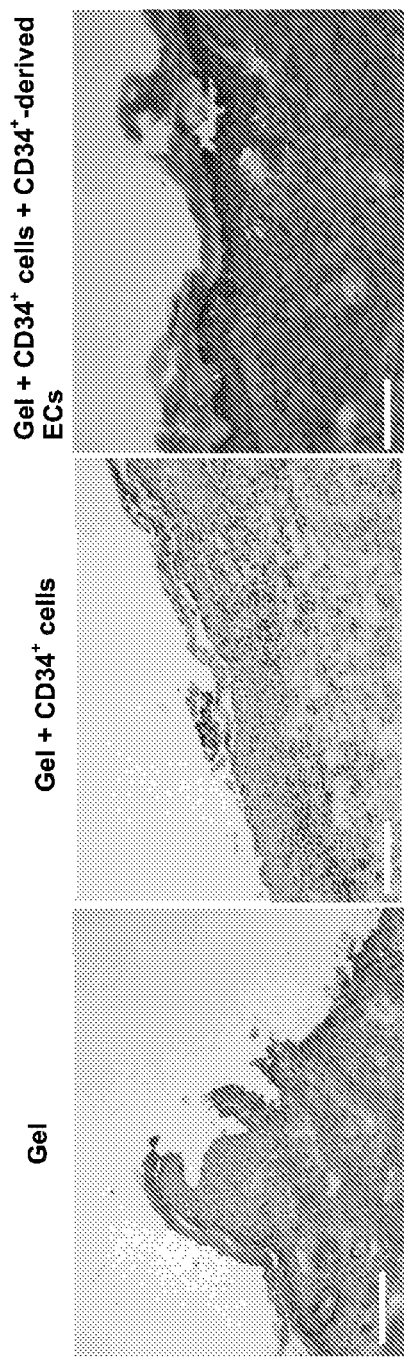
FIG. 14—Histological analysis of wounds treated by topical application of fibrin gel alone or fibrin gel containing CD34+ cells or CD34+ cells plus CD34+-derived ECs. Representative bright-field photographs of mouse wounds at day 10, stained with hematoxylin/eosin. Bar corresponds to 100 μm.
Figure 15:
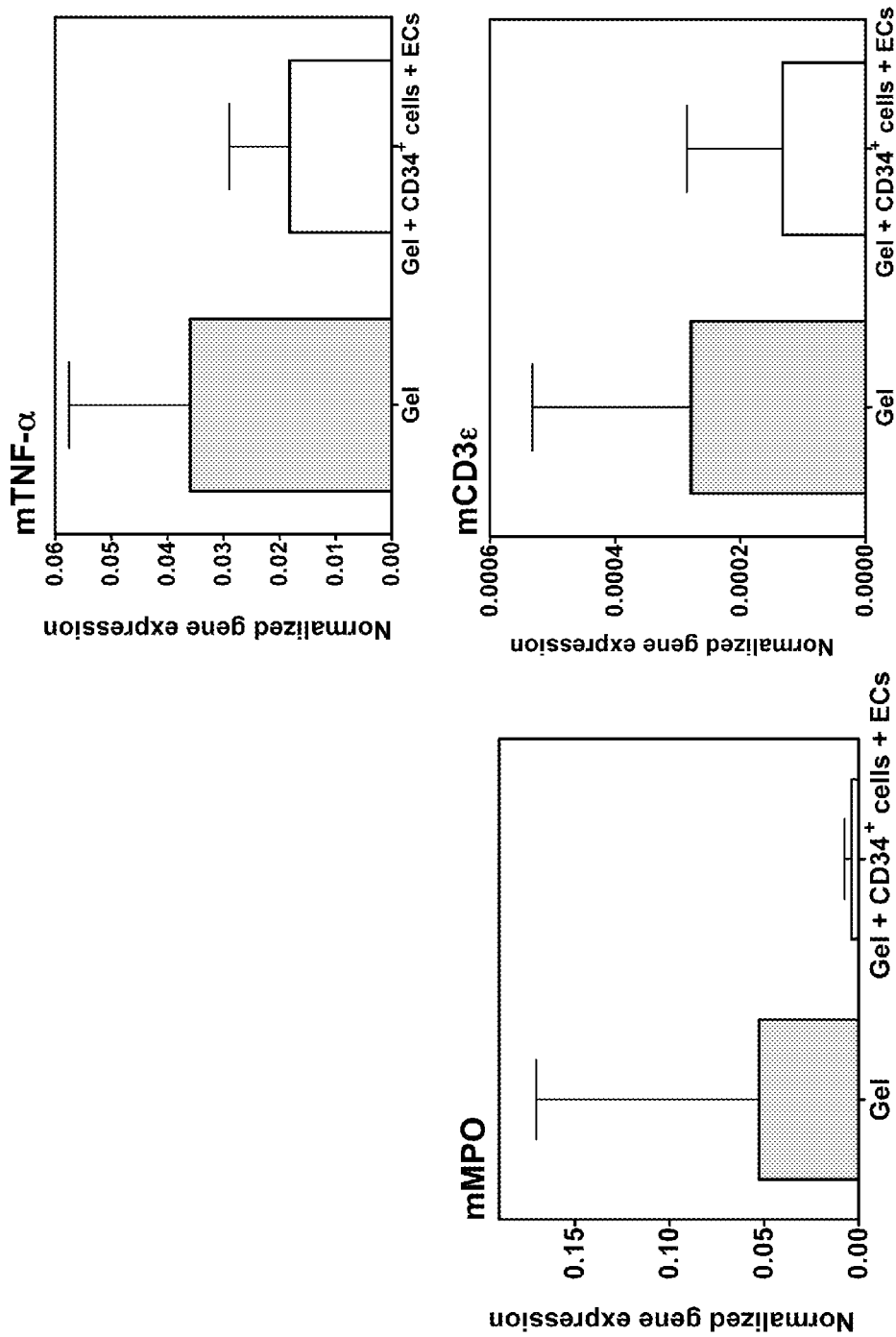
FIG. 15—Expression of inflammation-related genes by quantitative RT-PCR, on mouse wound skin biopsies at day 3. Wounds had been treated by topical application of fibrin gel containing $1\times10^5$ CD34+ cells and $0.35\times10^5$ CD34+-derived ECs. Control wounds were covered with gel only. Results are average±SD, n=9.

The invention discloses a therapeutic effect obtained by using a co-culture of Umbilical Cord Blood (UCB)-derived CD34+ cells encapsulated in a biomimetic gel, preferentially fibrin, to promote the healing, for example, of diabetic wounds and injuries caused ischemic and vascular diseases.

The invention is based on three components that can be isolated or derived from UCB: hematopoietic stem cells (CD34+ cells), CD34+-derived endothelial cells (ECs) to improve stem cell survival and coach their differentiation into vascular cells, and fibrin gel to retain both cells at the implant site.

The invention comprises two steps: first, stem cells (CD34+ cells) are differentiated into endothelial cells (ECs); second, the CD34+-derived endothelial cells are mixed with stem cells (CD34+ cells) in a fibrin gel precursor solution.

Prior to cell differentiation CD34+ cells are isolated from UCB. The samples are stored in sterile bags containing 35 mL of citrate-phosphate-dextrose anticoagulant solution. CD34+ cells are isolated from mononuclear cells, obtained from single or pooled UCB samples after Ficoll density gradient separation. CD34+ cells are positively selected (2 times) using the mini-MACS immunomagnetic separation system.

Regarding endothelial cell (EC) differentiation, isolated CD34+ cells are transferred onto 1% (w/v) gelatin-coated 24-well plates ($2\times10^5$ cells/well) and incubated in endothelial growth medium (EGM-2), supplemented with 18% (v/v) fetal bovine serum (FBS) and 50 ng/mL vascular endothelial growth factor ($VEGF_{165}$), at 5% $CO_2$, 37° C. After 5 days and then every other day, half of the volume of the medium is replaced with fresh one. At the end of the differentiation assay, expression of EC markers is evaluated by fluorescence activated cell sorting (FACS) and immunofluorescence staining. The functionality of the cells is evaluated by incubating the cells with acetylated low-density lipopoprotein (DiI-Ac-LDL).

The method could further comprise the fibrin gel preparation procedure. Cells [CD34+ cells (between $0.5\times10^5$ and $3\times10^5$), CD34+ cells ($1\times10^5$) in co-culture with CD34+-derived ECs ($0.35\times10^5$) or CD34+-derived ECs ($0.35\times10^5$)] are resuspended in the fibrin gel precursor solution (50 μL), preferably in 1 mL sterile syringes with cut tips. Polymerization is initiated at 37° C. and allowed to proceed over 30 min. After polymerization, the cell constructs are removed from the syringe and placed in 24-well plates containing specific medium, for up to 10 days.

In another embodiment of the invention, the fibrin gel is prepared by crosslinking fibrinogen obtained commercially in the presence of thrombin. In other cases, the fibrinogen can be isolated from a sample of patient's blood. In both cases, the fibrin gel comprises fibrinogen at a final concentration from about 1 mg/mL to about 100 mg/mL and thrombin at a final concentration from about 1 U/mL to about 500 U/mL. In a preferred embodiment, the fibrin gel comprises fibrinogen at a final concentration of 10 mg/mL and thrombin at a final concentration of 2 U/mL. In other cases, the fibrin gel is obtained from commercially available fibrin sealants, including Tisseel®, Tisseel VHSD® or Floseal®.

Another embodiment of the invention the stem cell is from autologous source. In another embodiment of the invention, the stem cell is from allogeneic source. In another aspect, the stem cells are positive for CD34 antigen—CD34+ cells.

Another aspect, the endothelial cells are derived from CD34+ cells. In various aspects, the CD34+ cells are present in a concentration from about $10\times10^2$ to about $10\times10^6$ cells per 1 mL of fibrin gel, and the ratio of CD34+ cells to CD34+-derived endothelial cells is between 10:1 to 0.5:1. In other aspects of the invention, the CD34+ cells are present in a concentration from about $10\times10^2$ to about $10\times10^6$ cells per 1 mL of fibrin gel, in the absence of CD34+-derived endothelial cells but in the presence of CD34+-derived endothelial cell conditioned medium.

In aspects of the invention, the fibrin gel precursor solution containing CD34+ cells and CD34+-derived endothelial cells is used to treat ischemic tissues, due to blood flow loss. Ischemia may occur as a consequence of cardiovascular diseases, diabetes, stroke, burn injury, macular degeneration, chronic wounds, among others. In another aspect of the invention, the fibrin gel precursor solution containing CD34+ cells and CD34+-derived endothelial cells is used to treat diabetic wounds.

CD34+-derived ECs co-cultured with CD34+ cells maximizes cell survival and contributes to the differentiation of CD34+ cells into ECs, improving the healing potential of the composition. The co-culture system, but not CD34+ cells or CD34+-derived ECs alone, can improve the healing kinetics in a diabetic animal model. The regenerative effect is mediated by both anti-inflammatory and pro-angiogenic processes. This co-culture approach might be used in other contexts to enhance the efficacy of stem cells and improve regeneration of different kinds of injuries.

This surprisingly effect involves the secretion of novel cytokines, including interleukin-17 (IL-17) and interleukin-10 (IL-10), and the activation of the ERK 1/2 pathway in CD34+ cells. This invention also show that the endothelial differentiation of CD34+ cells in co-culture with CD34+-derived ECs is mediated by a combination of soluble and insoluble factors. The regenerative potential of this co-culture system was demonstrated in a chronic wound diabetic animal model. The co-transplantation of CD34+ cells with CD34+-derived ECs improved the wound healing relatively to controls, by decreasing the inflammatory reaction and increasing the neovascularization of the wound.

The methods of the invention can be performed on any patient regardless of age or sex, although it is expected that elderly subjects may particularly benefit. As used herein, an elderly patient is one who is 60 years of age or older. It will be understood in the context of this description that the preferred subjects are mammal, more preferably human subjects.

Differentiation of UCB-Derived CD34$^+$ Cells into ECs

Results obtained by immunocytochemistry show that undifferentiated CD34$^+$ cells express high levels of CD34 (100%) and CD31 markers (85.46±17.0%, n=8), incorporate moderate levels of Ac-LDL (12.86±10.4%, n=13) and show no expression of the definitive endothelial marker vWF (1A). FACS analyses confirm their high expression of CD34 and CD31 markers, high expression of CD45, a typical marker of hematopoietic cells, and no expression of Flk-1/KDR and CD14 (a marker mainly expressed by macrophages) (1B). Similarly, no vWF expression and high CD34 expression were observed at gene level (2B). Therefore, the UCB-derived CD34$^+$ population used in this work is CD34$^+$ CD45$^+$ CD31$^+$ KDR2$^-$vWF$^-$CD14$^-$.

To differentiate CD34$^+$ cells into ECs, we cultured CD34$^+$ cells (10×10$^4$ cells per cm$^2$) in gelatin-coated dishes in EGM-2 medium with 20% (v/v) of FBS and 50 ng/mL of VEGF$_{165}$. Typically after 15-20 days of culture, CD34$^+$ cells attached to the culture dish with a cobblestone-like morphology and expressed high levels of EC markers, including CD31, CD34 and Flk-1/KDR over time (1C). In addition, differentiated CD34$^+$ cells stained positively for CD31 and VE-cadherin at cell-cell adherent junctions, produced vWF and were able to incorporate Ac-LDL (2A), typical markers found in ECs (8). In line with the EC phenotype, these cells do not express α-SMA, a smooth muscle cell marker (2A). Quantitative RT-PCR (qRT-PCR) analyses showed that CD34$^+$-derived ECs express the EC markers CD34 and vWF and produce angiogenic growth factors including VEGF, PlGF and bFGF (2B). The expression of PlGF growth factor is higher on CD34$^+$-derived ECs than on CD34$^+$ cells, while the opposite was observed for bFGF. In addition, qRT-PCR results show that the expression of angiogenic growth factors is higher on CD34$^+$-derived ECs than on HUVECs.

The ability of CD34$^+$-derived ECs to form cord-like structures was also assessed by culturing these cells in the basement membrane of a gelatinous protein mixture secreted by Engelbreth-Holm-Swarm (EHS) mouse sarcoma cells—Matrigel™. Similarly to HUVECs, CD34$^+$-derived ECs were able to spontaneously reorganize into cord-like structures when maintained in culture for 15 h (9). Yet, the angiogenesis potential of CD34$^+$-derived ECs is higher than that of HUVECs, as confirmed by the higher number of sprouts and network length (2C).

Fibrin gels have been shown to provide a permissive environment for endothelial cell adhesion, migration and three-dimensional organization (Bieche I et al., 2004, Hughes CG, 2008). However, it is unclear whether fibrin gels might be an effective substrate for CD34$^+$ cell adhesion. For this purpose, CD34$^+$ cells were plated on 24-well plates coated with fibrin gels or different substrates and cell adhesion evaluated by microscopy, by counting the cells attached after 3 h. CD34$^+$ cells demonstrated greater initial adhesion to fibrin gels than to polystyrene dishes, collagen and fibronectin (3). The number of CD34$^+$ cells adherent to fibrin was 2.0- (P,0.05), 4.0- (P,0.01) and 3.0-fold (P,0.01) greater than to collagen, polystyrene and fibronectin, respectively.

Next, we used fibrin gels to encapsulate CD34$^+$ cells. Initially, we studied the effect of cell number to gel volume for optimal cell survival. Cell viability did not change significantly after 10 days for the different cell densities tested (10). Therefore, 10×10$^4$ CD34$^+$ cells per 50 mL of fibrin gel were used in subsequent tests. Fibrin gels resist the degradation initiated by the metalloprotease enzymes released by CD34$^+$ cells, or CD34$^+$-derived ECs (3.5×10$^4$ cells), or the co-culture of CD34+ cells with CD34$^+$-derived ECs (10×10$^4$: 3.5×10$^4$ cells, respectively) for 10 days (11). Furthermore, cell traction does not reduce significantly the gel diameter over time in all the experimental groups (11).

Cell Survival is Improved by Co-Culturing CD34$^+$ Cells with CD34$^+$-Derived ECs CD34$^+$ cells encapsulated in fibrin gels have a viability of 60-70% at day 2 and day 10, statistically lower (n=6, P,0.001) than the one observed for CD34$^+$-derived ECs (4A). An MTT assay was used to determine the metabolic activity of cells encapsulated in the gels (4B). The metabolic activity of CD34$^+$ cells at day 10 was approximately 90% of the initial activity (day 2), suggesting that cells were in a non-proliferative state.

Quantitative LIVE/DEAD and MTT analyses indicate an important increase in cell viability and proliferation for CD34$^+$ cells co-cultured with CD34$^+$-derived ECs (n=6, P,0.01 or P,0.001) (4A,4B). This effect was observed for days 6 and 10, although more pronounced at day 10, in terms of metabolic activity. In contrast, HUVECs did not affect the viability of CD34$^+$ cells (n=6, P>0.05) (4C), indicating that the pro-survival effect is specifically mediated by CD34$^+$-derived ECs. Importantly, addition of CD34$^+$-derived EC-conditioned medium to cell constructs formed by CD34$^+$ cells resulted in an important increase in cell viability (n=6, P<0.001) (4C).

These results suggest that the pro-survival effect of CD34$^+$-derived ECs on CD34$^+$ cells is mediated, at least in part, by bioactive factors released from the ECs.

Phosphoinositide-3 kinase (PI3K)/Akt and mitogen activated protein kinase (MAPK)/extracellular signal regulated kinase 1/2(ERK 1/2) pathways regulate several cellular processes, including cell survival. Therefore, we analyzed the activation of Akt and ERK pathways on CD34$^+$ cells or CD34$^+$-derived ECs cultured in serum free-medium for 19 h and then treated with EC or CD34$^+$ cell-conditioned medium, respectively. The ratios between phosphorylated and total proteins were determined by a Multiplex assay (4D). Interestingly, the ERK but not the Akt pathway is activated in CD34$^+$ cells by EC-conditioned medium. Therefore, the pro-survival effect of EC-conditioned medium in CD34$^+$ cells seems to be mediated by the activation of the ERK pathway. On the other hand, no significant activation has been observed for ERK and Akt pathways in ECs by CD34$^+$-conditioned medium, as compared to the control.

To understand the crosstalk between both cells, we analysed the cytokines secreted by CD34$^+$ cells, CD34$^+$-derived ECs, or both cells encapsulated in fibrin gels, using a cytokine bead array (5). CD34$^+$-derived ECs encapsulated in fibrin gels secrete high levels (>100 pg/mL) of IL-6, IL-8, IL-13 and monocyte chemotactic activating factor (MCAF) (5A). On the other hand, CD34$^+$ cells encapsulated in fibrin gels secrete high levels (>100 pg/mL) of IL-8, IL-13 and MCAF (5B). Surprisingly, when both cells are encapsulated together in fibrin gels, they secrete high levels of the previous cytokines (IL-6, IL-8, IL-13 and MCAF) and two additional cytokines, IL-10 and IL-17 (5C).

CD34$^+$ Cell Adhesion to Fibrin Gels is Enhanced in the Presence of CD34$^+$-Derived ECs or EC Conditioned Medium To investigate the effect of the co-culture system in supporting CD34$^+$ cell adhesion, isolated CD34$^+$ cells (10× 10$^4$ cells/well) were cultured on top of fibrin gels (i) in the presence of CD34$^+$-derived ECs (3.5×10$^4$ cells/well), (ii) in the absence of ECs, or (iii) in the absence of ECs but in the presence of EC-conditioned medium. After 7 days in culture, the non-adherent cells were removed by washing and the adherent cells were counted by phase-contrast microscopy. 5.5±10.4% (n=17), 22.4±20.9% (n=15) and 44.2±33.2% (n=18) of $CD34^+$ cells were attached to the gel when cultured in the absence of ECs, in the presence of ECs, or in the absence of ECs but in the presence of EC-conditioned medium, respectively. The differences in $CD34^+$ cell recovery cannot be explained by differences in cell apoptosis/necrosis, since only a small fraction (below 10%) of the cells are affected by those (6A). However, cell apoptosis and necrosis are significantly discouraged (P<0.05) when the cells are cultured in EC-conditioned medium rather than basal medium.

$CD34^+$ Cell Differentiation into ECs is Enhanced in the Presence of $CD34^+$-Derived ECs Next, we assessed the potential of the co-culture system to support $CD34^+$ cell differentiation into ECs. For that purpose, $CD34^+$ cells ($10\times10^4$ cells/well) were cultured on top of fibrin gels (i) in the presence of $CD34^+$-derived ECs ($3.5\times10^4$ cells/well), (ii) in the absence of ECs, or (iii) in the absence of ECs but in the presence of EC-conditioned medium. After 7 days in culture, the ability of the cells to take up Ac-LDL, an endothelial marker, was evaluated by fluorescence microscopy (6B). Uptake of DiI-labeled Ac-LDL increased from 12% on isolated $CD34^+$ cells to 70% after differentiation in the presence of $CD34^+$-derived ECs (P<0.001). A non-statistically significant increase was observed for Ac-LDL expression on $CD34^+$ cells cultured on fibrin without cells (basal medium, 7 days), compared to original $CD34^+$ cells (time zero). Therefore, the results indicate that $CD34^+$ cell differentiation into ECs is significantly improved in the presence of $CD34^+$-derived ECs. Because no statistical increase in Ac-LDL uptake was observed for $CD34^+$ cells cultured in EC conditioned medium, the endothelial differentiation of $CD34^+$ cells is likely mediated by a combination of soluble and insoluble factors. We also evaluated by qRT-PCR the differentiation of $CD34^+$ cells in co-culture with ECs and encapsulated in fibrin gels (6C). The expression of EC markers (vWF and CD34) was similar or higher than for ECs or $CD34^+$ cells encapsulated in fibrin gels, indicating that most of the cells in the gels express endothelial markers.

Co-Transplantation of $CD34^+$ Cells with $CD34^+$-Derived ECs Improve Wound Healing in Diabetic Mice The therapeutic effect of our tissue engineering approach was further evaluated in a chronic wound animal model. Wounds were created at the anterior and posterial dorsal regions of streptozotocin-induced diabetic mice. One of the wounds was covered with fibrin gel alone to serve as internal control, whereas the other wound was covered with either gel containing $1\times10^5$ $CD34^+$ cells or $1\times10^5$ $CD34^+$ cells with $0.35\times10^5$ ECs derived from $CD34^+$ cells (7A). At day 3 postwounding, the wound area was statistically lower in wounds treated with the gel containing a coculture of $CD34^+$ cells with ECs compared to wounds treated with PBS (P<0.05, n=6), indicating improved closure kinetics. No statistical difference was observed for the remaining experimental groups against the control (P>0.05, n=6). At day 10, although not statistically different, wounds treated with the gel containing the co-culture of cells showed a greater area reduction compared to wounds treated with PBS. Such differences between the experimental group and control group were not observed for the remaining groups.

We next evaluated the survival of the transplanted cells using a non-invasive real time fluorescence imaging (CellVizio). At day 3, cell survival was low (8.9±11.7%, n=4) in mice treated with a co-culture of $CD34^+$ and $CD34^+$-derived ECs. At day 10, qRT-PCR analyses of excised wounds showed the absence of human cells (data not shown). This suggests that the therapeutic effect of the cell co-culture is likely produced at the early phases of the healing process.

Co-Transplantation of $CD34^+$ Cells with $CD34^+$-Derived ECs Increases Early Neovascularization and Decreases Inflammatory Processes Because stem cells and progenies can contribute for the regeneration of the tissues through neovascularization, we assessed the capillary density by immunofluorescence using vWF as a vascular marker, at day 3 (7B). A significant increase in the density of microvessels was observed for the experimental groups containing stem cells relatively to the group of the gel alone (P<0.001). This indicates that part of the regenerative effect might be mediated through a neovascularization process.

The regenerative effect of stem cells and their progenies might be also mediated by a reduction of inflammation at the wound site. Therefore, the expression of inflammatory markers was assessed by qRT-PCR. Myeloperoxidase (MPO), CD3ε and tumor necrosis factor-alpha (TNF-α) are markers for the presence of neutrophils, T cells and inflammatory cytokines, respectively. Although not statistically significant (P>0.05, n=9), the inflammatory reaction (considering all three markers) in the wounds treated with gel containing a co-culture of $CD34^+$ cells and $CD34^+$-derived ECs (12) was reduced compared to the control, i.e. wounds treated with the gel alone. This effect was further confirmed at protein level, by a multiplex assay (7). In line with previous studies (May WS, 2000), IL-1β, TNF-α, IL-6 and GM-CSF are expressed in all experimental groups at early stages during the healing process. However, the secretion of TNF-α was statistically (P<0.05) higher in wounds with gel alone than in wounds treated with gel encapsulating $CD34^+$ and $CD34^+$-derived ECs or $CD34^+$ cells alone (7B). These results indicate that stem cells and their progenies are able to attenuate the inflammatory process at the site of injury, contributing to the healing progression.

This invention is based on three components that can be isolated or derived from UCB: hematopoietic stem cells ($CD34^+$ cells), $CD34^+$-derived ECs to improve stem cell survival and coach their differentiation into vascular cells, and fibrin gel to retain both cells at the implant site. We show that diabetic chronic wounds treated with a combination of both types of cells encapsulated in a fibrin gel have improved healing compared to wounds treated with gel containing only stem cells.

Our results indicate that fibrin gels support higher CD34+ cell adhesion than collagen gels, fibronectin or tissue culture polystyrene. Fibrin gels obtained by the crosslinking of fibrinogen by thrombin, two plasma-derived components, have RGD and AGDV sites through which they can interact with cell integrins.

ECs differentiated from UCB-derived $CD34^+$ cells have superior angiogenic properties than primary ECs (HUVECs). This is confirmed by their ability to secrete higher levels of angiogenic factors, including VEGF, PlGF and bFGF, and to produce a higher number of sprouts and larger network in a gelatinous protein mixture secreted by Engelbreth-Holm-Swarm (EHS) mouse sarcoma cells—Matrigel™ (2). This seems to be specific for ECs derived from cord blood, since peripheral blood-derived human endothelial progenitor cells have similar angiogenic properties as HUVECs.

When both $CD34^+$ cells and $CD34^+$-derived ECs are encapsulated in fibrin gels, they crosstalk, as confirmed by the secretion of specific cytokines. $CD34^+$-derived ECs encapsulated alone in fibrin gels secreted high levels of IL-6, IL-8, IL-13 and MCAF, while CD34$^+$ cells encapsulated alone in fibrin gels produced high levels of IL-8, 11-13 and MCAF.

When both types of cells were concurrently encapsulated in fibrin gels, they secreted two novel cytokines, cytokine IL-17 and IL-10, in addition to the ones secreted by each type of cell. IL-17 is a cytokine that has been reported to be produced by T lymphocytes and monocytes (CD 14$^+$ cells). The binding of IL-17 in ECs stimulates the production of IL-6, IL-8, transforming growth factor β (TGF-β) and MCAF and stimulates EC migration and tube formation. IL-10 is a cytokine produced by various cell populations, including CD34$^+$ cells and ECs. IL-10 activity is mediated by its interaction with the IL-10 receptor, expressed on a variety of cells, including CD34$^+$ cells and ECs. In our study, it is unclear whether IL-10 was secreted by CD34$^+$ cells or CD34$^+$-derived ECs and whether IL-10 is acting on either both cells or only one type of cells. Importantly, it has been reported that IL-10 increases Bcl-2 expression and survival in CD34$^+$ cells In this study, we show that the adhesion, viability, proliferation and vascular differentiation of CD34$^+$ cells in fibrin gels are improved it order to enhance, for example wound healing by co-culturing these cells with CD34$^+$-derived ECs. Importantly, the pro-survival effect is specific for CD34$^+$-derived ECs, since primary ECs (HUVECs) have no such effect. Our results also indicate that CD34$^+$ cell survival, proliferation and adhesion to fibrin gels are most likely mediated by biomolecules secreted by CD34$^+$-derived ECs, since conditioned medium collected from these cells has similar inductive effects. However, CD34$^+$ cell differentiation into ECs is likely mediated by a combination of soluble and insoluble factors, since CD34$^+$-derived EC-conditioned medium alone does not improve CD34$^+$ cell differentiation. The improved adhesion and viability of CD34$^+$ cells in the presence of CD34$^+$-derived ECs is likely mediated by growth factors and cytokines. VEGF, IL-3, IGF-I and IL-10 have been reported to be involved in the survival of CD34$^+$ cells. We show that VEGF is highly expressed at gene level both in CD34$^+$ cells and in CD34$^+$-derived ECs encapsulated in fibrin gels (7), and thus might account for the improved survival of CD34$^+$ cells. Another factor that might contribute to the survival of CD34$^+$ cells is IL-10 (see above). In this invention we find that the improved adhesion of CD34$^+$ cells in the presence of ECs is mediated by soluble factors. It has been shown that binding of soluble P-selectin, expressed by ECs, to P-selectin glycoprotein ligand-1 (PSGL-1), expressed by CD34$^+$ cells, activates cellular adhesion molecules on CD34$^+$ cells, particularly αvβ5 integrins. The expression of these integrins favors the adhesion to fibrinogen (Weisel J W, 2009). A similar mechanism might explain the improved cellular adhesion in our co-culture system.

CD34$^+$-derived ECs, but not medium conditioned by these cells, rapidly induce the differentiation of CD34$^+$ cells into ECs. CD34$^+$ cells cultured for 7 days in the presence of CD34$^+$-derived ECs are able to uptake DiI-labeled Ac-LDL (70% of the cells), a functional feature of ECs.

These results suggest an early involvement of cell-cell interactions or extracellular matrix synthesized by ECs in the induction of vascular differentiation. Yet, the induction mechanism is still unknown. Interestingly, induction of vascular differentiation by extracellular matrix produced by ECs has been described recently for mesenchymal stem cells (Vellenga E et al., 2009).

Embodiments

Materials and Methods
Staining of Live Cells with Fluorescent Dyes

Cells were ressuspended in serum-free medium (M199) at a density of 1×10$^6$ cells/mL and 5-10 μL of the dye [5(6)-carboxyfluorescein diacetate N-succinimidyl ester (CFSE; Sigma-Aldrich) or Vybrant® DiD cell-labeling solution, preferably from Invitrogen was added per mL of cell suspension, mixing well by gentle pipetting. After incubation at 37° C. for up to 30 minutes, the labeled cell suspension was centrifuged, the supernatant removed and the cells ressuspended in warm (37° C.) M199 medium. The cells were then washed twice in warm medium and finally ressuspended in the culture medium of choice. For cells adherent to culture plates or flasks, a similar procedure was followed, with the required adjustments. CFSE forms green fluorescent conjugates on deacetylation, whilst DiD-labeled cells display red fluorescence.

Gelatinous Protein Mixture Secreted by Engelbreth-Holm-Swarm (EHS) Mouse Sarcoma Cells—Matrigel™ Assay A 24-well plate was coated with 0.4 mL of a gelatinous protein mixture secreted by Engelbreth-Holm-Swarm (EHS) mouse sarcoma cells—as for example Matrigel™, from BD Biosciences, per well and incubated for 30 minutes at 37° C. Either CD34$^+$-derived endothelial cells (passage 4) or HUVECs were seeded on top of the polymerized said Matrigel™ at a concentration of 1×10$^5$ per 300 μL of EGM-2 medium. The cells were either unlabeled or previously labeled with CFSE or Vybrant® DiD. After 1 h of incubation at 37° C., 1 mL of EGM-2 was added. Cord formation was evaluated by phase contrast microscopy, preferably Zeiss Axiovert 40C from Carl Zeiss International, 15 or 48 h after cell seeding.

Preparation of Fibrin Gels

Fibrin gels were formed by crosslinking of fibrinogen in the presence of thrombin, preferably both from Sigma-Aldrich). The fibrinogen solution was prepared by dissolving human fibrinogen in Tris-buffered saline (TBS), pH 7.4 (20 mg/mL), and then sterilized by filtering through a 0.22 μm syringe filter, preferably of Acrodisc. Fresh thrombin solutions were prepared by dissolving human thrombin in TBS at pH 7.4 at a concentration of 50 U/mL. Fibrin gels (50 μL, unless otherwise stated) were prepared by mixing three different components: fibrinogen (10 mg/mL), CaCl$_2$, preferably from Merck (2.5 mM) and thrombin (2 U/mL). This solution was allowed to gel at 37° C. and 100% relative humidity.

Degradation of Fibrin Gels

Gel precursor solution was prepared by mixing, preferably, Alexa Fluor® 488 human fibrinogen conjugate, preferably from Invitrogen (0.156 mg) to unlabeled fibrinogen (9.844 mg) in 1 mL of TBS. The degradation rate of fibrin gels with or without cells over time was indirectly estimated by the decrease of their fluorescence. Their fluorescence was measured immediately at time zero and at the desired time points. Complete degradation of the gels was induced by incubation with 200 μL of a solution of human plasmin preferably from Sigma-Aldrich in TBS (0.006 U per gel) for an overnight at 37° C. Following centrifugation, the fluorescence of the supernatant fractions was measured at 520 nm in a SPECTRAmax Gemini EM fluorescence microplate reader, preferably from Molecular Devices.

Viability and Metabolic Activity of Cell Constructs

Cell viability of cell constructs was determined using a LIVE/DEAD kit, preferably from Invitrogen. The gels containing the encapsulated cells were washed in PBS, immersed in a working solution of 2 μg/mL calcein AM and 4 μg/mL ethidium homodimer-1 in PBS for 30 minutes at 37° C. and visualized under a Zeiss Axiovert 200M fluorescence inverted microscope.

The metabolic activity of cell constructs was measured through a 3-(4,5-dimethylthiazol-2-yl)-2,5-diphenyl tetrazolium bromide, preferably MTT from Sigma-Aldrich assay after 2, 6 and 10 days of culture. The MTT solution (1 mL, 0.5 mg/mL in the same type of medium in which the cells had been cultured) was added to each well containing the cell constructs and incubated for 4 h, at 37° C. After that time, the cell constructs were placed in 1.5 mL polypropylene tubes and 0.15 mL of dymethyl sulfoxide, preferably DMSO from Merck, was added. The constructs were broken apart using a tissue homogeneizer, to release the formazan crystals formed by cells presenting mitochondrial metabolic activity. The formazan crystals were solubilized in the DMSO and their absorbance measured spectrophotometrically at 540 nm, in a microplate spectrophotometer, preferably PowerWave XS from BioTek.

FACS Analysis

Cells were dissociated from the culture plate by exposure to Cell Dissociation Buffer, preferably from Invitrogen for 5-10 minutes and gentle pipetting, centrifuged and finally ressuspended in PBS supplemented with 5% (v/v) FBS. The single cell suspensions were aliquoted ($1.25-2.5 \times 10^5$ cells per condition) and stained with either isotype controls or antigen-specific antibodies: anti-human PECAM1-FITC, preferably from BD Biosciences Pharmingen, CD14-FITC, CD34-PE, CD45-FITC, preferably all from Miltenyi Biotec and KDR/Flk1-PE, preferably from R&D Systems. Cells were analyzed without fixation on a FC500 flow cytometer, preferably from Coulter, using propidium iodide (7-AAD Viability staining solution; preferably from, bioNova cientifica) to exclude dead cells. Data analysis was carried out using Coulter FC Analysis software.

Immunostaining

Cells were fixed with 4% (v/v) paraformaldehyde, preferably from EMS for 15-20 minutes at room temperature. After permeabilizing the cells with 0.1% (v/v) Triton X-100, preferably from Sigma-Aldrich for 10 minutes, whenever required, and blocking for 30 minutes with 1% (w/v) bovine serum albumin (BSA) solution preferably from Sigma-Aldrich, the cells were stained for 1 h with the following primary mouse anti-human monoclonal antibodies: PECAM1, CD34, von Willebrand factor (vWF), α-smooth muscle actin (α-SMA), smooth muscle myosin heavy chain (SM-MHC), preferably all all from Dako and VE-cadherin (VE-CAD), preferably from Santa Cruz Biotechnology. In each immunofluorescence experiment, an isotype-matched IgG control was used. The binding of primary antibodies to specific cells was detected with anti-mouse IgG Cy3 conjugate, preferably from Sigma-Aldrich. The nucleus of cells was stained with 4',6-diamidino-2-phenylindole, preferably from Sigma-Aldrich. After the indirect labelling, the cells were examined with a Zeiss fluorescence microscope.

For uptake of DiI-labeled acetylated low-density lipoprotein (DiI-Ac-LDL), cells were incubated with 10 μg/mL DiI-labeled Ac-LDL for 4 h at 37° C. After incubation, cells were washed three times in EGM-2, fixed with 4% (v/v) paraformaldehyde for 30 min and visualized in a fluorescence microscope.

Quantitative Reverse Transcription-Polymerase Chain Reaction (qRT-PCR) Analysis

Cell constructs were frozen and ground to a fine powder in a cold mortar, under liquid N2, transferred to polypropylene tubes, homogenyzed in Trizol reagent, preferably from Invitrogen and total RNA was extracted by using the RNeasy Mini Kit, preferably from Qiagen, according to manufacturer's instructions. When the starting material was frozen mouse skin, tissue samples were disrupted in Trizol in 2 mL tubes containing a 5 mm diameter stainless steel bead, preferably from Qiagen, in a TissueLyser II apparatus, preferably from Qiagen for 2 min, at 30 Hz (twice). When starting from a cell suspension, cells were centrifuged and homogenized in Trizol. In all cases, cDNA was prepared from 1 μg total RNA using Taqman Reverse transcription reagents, preferably from Applied Biosystems. Quantitative PCR (qPCR) was performed using Power SYBR Green PCR Master Mix, preferably from Applied Biosystems and the detection was carried out in a 7500 Fast Real-Time PCR System, preferably from Applied Biosystems. Quantification of target genes was performed relatively to the reference (human or mouse, depending on the type of cells under analysis) GAPDH gene: relative expression=$2[-(Ctsample-CtGADPH)]$. The mean minimal cycle threshold values (Ct) were calculated from four independent reactions. Primer sequences are published as supporting information (16).

Cytokine Secretion Analyses

Cell culture supernatants and protein isolates were evaluated for the presence and concentrations of cytokines using either a Bio-Plex Pro Human Cytokine 17-Plex Panel Assay or a Bio-Plex Pro Mouse Cytokine 8-Plex Assay, preferably both from Bio-Rad, Hercules, Calif., USA, according to manufacturer's instructions, in a Bio-Plex 200 System, preferably from Bio-Rad. The human Group I 17-Plex Panel consisted of the following analytes: interleukin-1β (IL-1β), IL-2, IL-4, IL-5, IL-6, IL-7, IL-8; IL-10, IL-12 (p70), IL-13, IL-17, granulocyte colony-stimulating factor (G-CSF), granulocyte/macrophage colony-stimulating factor (GM-CSF), interferon-γ (IFN-γ), monocyte chemotactic protein (monocyte chemotactic activating factor [MCP-1 (MCAF)], macrophage inflammatory protein-β (MIP-1 β) and tumor necrosis factor-α (INF-α). The mouse group I 8-Plex panel comprised the following analytes: IL-1 β, IL-2, IL-4, IL-5, IL-10, GM-CSF, IFN-γ and INF-α. A mouse Singleplex/x-Plex IL-6 Bead Region was combined to these analytes. Supernatant media samples were collected, centrifuged to remove precipitates and frozen. Proteins were isolated from frozen mouse skin tissue samples that were disrupted in a TissueLyser II apparatus, preferably from Qiagen for 2 min, at 30 Hz (twice), by using the Bio-Plex Cell Lysis kit, preferably from Bio-Rad, according to the manufacturer's recommendations. A standard range of 0.2 to 3.200 pg/mL was used. Samples and controls were run in triplicate, standards and blanks in duplicate.

Analysis of Total and Phosphorylated Akt and ERK Protein Levels

Activation of Akt and extracellular signal-regulated kinase (ERK) in $CD34^+$ cells and $CD34^+$-derived ECs was promoted by starving the cells for 19 h in serum-free M199 medium, with Earle's Salts, L-glutamine, preferably from Sigma-Aldrich and then treating them for 10 minutes, by replacing the medium by cell-conditioned M199 or fresh M199. Conditioned M199 used for $CD34^+$ cell treatment had been obtained by culturing ECs in M199 for 24 h ($0.75 \times 10^5$ cells per mL of medium), removing the medium and sterilizing it by filtration. Conditioned M199 used for EC treatment had been obtained by culturing $CD34^+$ cells in M199 for 24 h ($2 \times 10^5$ cells per mL of medium), removing the medium and sterilizing it by filtration. Following treatment, proteins were isolated from the cells, either adherent to plates or in suspension, using the Bio-Plex Cell Lysis kit, preferably from Bio-Rad, according to the manufacturer's recommendations. The levels of Akt and ERK phosphorylation were determined using Bio-Plex kits from Bio-Rad, according to manufacturer's instructions.

Determination of Apoptosis and Necrosis in $CD34^+$ Cells

To determine $CD34^+$ apoptosis and necrosis, $0.30 \times 10^5$ $CD34^+$ cells were cultured on top of 500 µL fibrin gels, in 24-well plates, in either EGM-2 medium or EGM-2 conditioned by ECs. After 7 days of culture, cell apoptosis/necrosis was assessed using the Vybrant® Apoptosis Assay Kit #3 (FITC annexin V/propidium iodide, preferably from Invitrogen, according to manufacturer's recommendations. This assay detects the externalization of phosphatidylserine in apoptotic cells. In normal live cells, phosphatidylserine is located on the cytoplasmatic surface of the cell's membrane. Propidium iodide stains necrotic cells with red fluorescence.

Animals

All protocols in this study were approved by the Ethics Committee of the Faculty of Medicine of the University of Coimbra. Male C57BL/6 wild-type mice (10-12 week-old), purchased from Charles River, preferably from Wilmington) and weighing between 20 and 30 g, were housed in a conventional animal facility on a 12 h light/12 h dark regimen and fed a regular chow ad libitum.

1—Induction of Diabetes and Dermal Wounds

Diabetes mellitus was induced in mice by a single intraperitoneal injection of 150 mg/kg of streptozotocin, preferably from Sigma-Aldrich, in 200 µL citrate buffer, pH 4.2, and the animals were used 6-8 weeks after induction of a diabetic metabolic state. Glycemia was weekly monitored after STZ treatment with a glucometer with glucose test strips, preferably Accu-Chek Aviva, Roche and only animals with blood glucose levels greater than 300 mg/dL were used in this study. Insulin (16-32 U/Kg or 0.4-0.8 U/mouse, Sigma-Aldrich) was injected only for weight maintenance. To evaluate wound healing response to treatment with stem cells in scaffolds, mice were subjected to the creation of dermal wounds 6-8 weeks following diabetes induction. The animals were anesthetized by intramuscular injection of a xylazine/ketamine solution [ketamine hydrochloride, 10 mg/mL, preferably Imalgene, 50 mg/kg of body weight, and xylazine hydrochloride, 2 mg/mL, preferably from Rompun®, 10 mg/kg of body weight] and allowed to recover on a hot pad (37° C.). The hair was shaved in the dorsolumbar skin and two 6 mm-diameter full-thickness excisional wounds, extending to the adipose tissue, were performed with a sterile biopsy punch, after disinfecting the area with a povidone-iodine solution, preferably Betadine®. The wounds were longitudinally aligned and separated by a sufficient amount of non-wounded skin.

2—Wound Treatment

The putative therapeutic effect of stem cells and their progenies encapsulated in fibrin gels on wound healing was assessed by a single topical application of the treatment of choice on the wounds immediately after they were created. In each animal, a 25 µL fibrin gel precursor containing $1 \times 10^5$ human umbilical cord blood $CD34^+$ cells, either alone or in combination with $0.35 \times 10^5$ $CD34^+$-derived endothelial cells, or $0.35 \times 10^5$ $CD34^+$-derived ECs, was applied on one of the wounds, in either the top (in half of the animals) or in the bottom position, and allowed to polymerize, whereas on the other wound only fibrin gel without cells (in some experimental groups) or PBS (in the remaining groups) was applied, as an internal control. All cells had been previously labelled with CFSE.

The progress of wound closure was monitored by measuring the wound area. To determine the rate of wound closure, the excision wounds were traced on a transparent paper having a millimeter scale, wound areas evaluated using computer imaging analysis, preferably AxioVision 4.8, and the change in wound area was calculated as the percentage of wound area that had healed. Measurements were done immediately after wounding, as well as one, three, five, eight and 10 days later. The wounds were photographed at the same time points.

In vivo bio-distribution of cells at day 0 and day 3 was monitored by noninvasive fiber-based confocal microscopy, preferably CellVizio®. The S-1500 optical probe used for image acquisition has a diameter of 1.5 mm, providing images immediately below the surface of biological tissue, with a slice thickness of 15 µm and a lateral resolution of 5 µm. Fluorescent-labeled cells localized in the wounds were quantified in at least 3 mice.

3—Analyses of Excision Wounds

Animals were anesthetized and sacrificed by cervical dislocation either on the third or tenth day post-wounding and 10 mm-diameter skin biopsy specimens, centered on the wound bed and comprising the wound margins, were collected.

Each biopsy sample was cut in two halves, one of which was embedded in cryomolds filled with O.C.T. preferably Tissue Tek®/Shandon Cryomatrix®; from Thermo Fisher Scientific, Waltham, frozen in dry-ice and cryopreserved at −70° C., whereas the other half was snap-frozen in liquid nitrogen and also stored at −70° C. O.C.T.-embedded samples were serially sectioned in 7 µm slices in a Leica CM3050 S cryostat, preferably Leica, Wetzlar, cooled to −20° C., and some were immunostained for vWF to determine total capillary density (human and mouse). Staining with rabbit anti-vWF (1:300; preferably from Dako) was followed by goat Cy3-conjugated anti-rabbit IgG (1:60; preferably from Sigma-Aldrich). qPCR analysis was performed on the remaining skin biopsy samples, to determine the total number of human cells. Other sections underwent histological staining with hematoxylin and eosin (H&E).

The invention is of course not in any way restricted to the embodiments described and a person with ordinary skill in the art will foresee many possibilities to modifications thereof without departing from the basic idea of the invention as defined in the appended claims.

The following claims set out particular embodiments of the invention.

The invention claimed is:

1. A composition comprising a co-culture of:
   a) a population of CD34$^+$ hematopoietic stem cells derived from human umbilical cord blood; and
   b) a population of CD34$^+$ endothelial cells derived from said CD34$^+$ hematopoietic stem cells, wherein a) and b) are encapsulated in a fibrin gel and
wherein the ratio of said CD34$^+$ hematopoietic stem cells to said CD34$^+$ endothelial cells is between 0.5:1 and 10:1 and wherein the co-culture secretes IL-10 and IL-17.

2. The composition according to claim 1 further comprising an excipient.

3. The composition according to claim 1, wherein the fibrin gel is prepared by crosslinking fibrinogen in the presence of thrombin, and wherein the fibrin gel comprises fibrinogen at a concentration from 1-100 mg/ml and thrombin at a concentration from 1-500 U/ml.

4. The composition according to claim 3, wherein the fibrin gel comprises fibrinogen at a concentration from 10-30 mg/ml and thrombin at a concentration from 2-50 U/ml.

5. The composition according to claim 1, wherein the population of the CD34$^+$ hematopoietic stem cells comprises autologous cells, allogeneic cells or a mixture thereof.

6. The composition according to claim 1, comprising CD34$^+$ hematopoietic stem cells in a concentration from $10 \times 10^2$ to $10 \times 10^6$ cells per 1 mL of fibrin gel, wherein the ratio of CD34$^+$ hematopoietic stem cells to CD34$^+$ endothelial cells is between 10:1 and 5:1.

7. The composition according to claim 1, wherein the CD34$^+$ hematopoietic stem cells are present in a concentration of $4.0 \times 10^6$ cells per 1 mL of a fibrin gel.

8. The composition according to claim 1, wherein the ratio of CD34$^+$ hematopoietic stem cells to CD34$^+$ endothelial cells is between 0.5:1 and 3:1.

9. The composition according to claim 1, further comprising VEGF$_{165}$ at a concentration in the range of about 30 ng/mL to 100 ng/mL.

10. The composition according to claim 1 further comprising any of collagen I, collagen IV, laminin, fibrin, fibronectin, a proteoglycan, a glycoprotein, a glycoaminoglycan, a proteinase, a collagenase, a chemotactic agent, or a growth factor.

11. The composition according to claim 10, comprising a growth factor selected from the group consisting of: VEGF, VEGF$_{165}$, PDGF, angiopoietin-Ang, ephrin-Eph, fibroblast growth factor-FGF, placental growth factor-PlGF, transforming growth factor β-1 (TGF-β1), cytokines, erythropoietin, thrombopoietin, transferring, insulin, stem cell factor (SCF), granulocyte colony-stimulating factor (G-CSF), granulocyte-macrophage colony stimulating factor (GM-CSF) and any mixture of any of the foregoing.

12. The composition according to claim 9, wherein the concentration of VEGF$_{165}$ is 50 ng/mL.

13. The composition according to claim 1, wherein the fibrin gel comprises a concentration of Fetal Bovine Serum (FBS) between 15% and 20% (v/v).

14. The composition according to claim 1, wherein the composition is in the form of a topical formulation or an injectable formulation.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Homo sapiens

<400> SEQUENCE: 1

-continued

```
tgaagcctag cctgtcacct                                               20

<210> SEQ ID NO 2
<211> LENGTH: 20
<212> TYPE: DNA
<213> ORGANISM: Homo sapiens

<400> SEQUENCE: 2
cgcacagctg gaggtcttat                                               20

<210> SEQ ID NO 3
<211> LENGTH: 20
<212> TYPE: DNA
<213> ORGANISM: Homo sapiens

<400> SEQUENCE: 3
atgttgtggg agatgtttgc                                               20

<210> SEQ ID NO 4
<211> LENGTH: 20
<212> TYPE: DNA
<213> ORGANISM: Homo sapiens

<400> SEQUENCE: 4
gcagataaga gctcagcctt                                               20

<210> SEQ ID NO 5
<211> LENGTH: 20
<212> TYPE: DNA
<213> ORGANISM: Homo sapiens

<400> SEQUENCE: 5
agaaggagga gggcagaatc                                               20

<210> SEQ ID NO 6
<211> LENGTH: 21
<212> TYPE: DNA
<213> ORGANISM: Homo sapiens

<400> SEQUENCE: 6
acacaggatg gcttgaagat g                                             21

<210> SEQ ID NO 7
<211> LENGTH: 20
<212> TYPE: DNA
<213> ORGANISM: Homo sapiens

<400> SEQUENCE: 7
acgtggagct gacgttctct                                               20

<210> SEQ ID NO 8
<211> LENGTH: 20
<212> TYPE: DNA
<213> ORGANISM: Homo sapiens

<400> SEQUENCE: 8
cagcaggagt cactgaagag                                               20

<210> SEQ ID NO 9
<211> LENGTH: 20
<212> TYPE: DNA
<213> ORGANISM: Homo sapiens
```

```
<400> SEQUENCE: 9
aagcaggagg atcgcttgag                                              20

<210> SEQ ID NO 10
<211> LENGTH: 20
<212> TYPE: DNA
<213> ORGANISM: Homo sapiens

<400> SEQUENCE: 10
tgaagcctag cctgtcacct                                              20

<210> SEQ ID NO 11
<211> LENGTH: 20
<212> TYPE: DNA
<213> ORGANISM: Homo sapiens

<400> SEQUENCE: 11
agccacatcg ctcagacacc                                              20

<210> SEQ ID NO 12
<211> LENGTH: 19
<212> TYPE: DNA
<213> ORGANISM: Homo sapiens

<400> SEQUENCE: 12
gtactcagcg ccagcatcg                                               19

<210> SEQ ID NO 13
<211> LENGTH: 20
<212> TYPE: DNA
<213> ORGANISM: Mouse sarcoma

<400> SEQUENCE: 13
gctacccgct tctccttctt                                              20

<210> SEQ ID NO 14
<211> LENGTH: 20
<212> TYPE: DNA
<213> ORGANISM: Mouse sarcoma

<400> SEQUENCE: 14
ttgcgaatgg tgatgttgtt                                              20

<210> SEQ ID NO 15
<211> LENGTH: 20
<212> TYPE: DNA
<213> ORGANISM: Mouse sarcoma

<400> SEQUENCE: 15
cactctgggc ttgctgatgg                                              20

<210> SEQ ID NO 16
<211> LENGTH: 23
<212> TYPE: DNA
<213> ORGANISM: Mouse sarcoma

<400> SEQUENCE: 16
tcatagtctg ggttgggaac agg                                          23

<210> SEQ ID NO 17
<211> LENGTH: 25
<212> TYPE: DNA
<213> ORGANISM: Mouse sarcoma
```

```
<400> SEQUENCE: 17
catcttctca aaattcgagt gacaa                                          25

<210> SEQ ID NO 18
<211> LENGTH: 22
<212> TYPE: DNA
<213> ORGANISM: Mouse sarcoma

<400> SEQUENCE: 18
gggagtagac aaggtacaac cc                                             22

<210> SEQ ID NO 19
<211> LENGTH: 20
<212> TYPE: DNA
<213> ORGANISM: Mouse sarcoma

<400> SEQUENCE: 19
accacagtcc atgccatcac                                                20

<210> SEQ ID NO 20
<211> LENGTH: 20
<212> TYPE: DNA
<213> ORGANISM: Mouse sarcoma

<400> SEQUENCE: 20
tccaccaccc tgttgctgta                                                20
```